(12) United States Patent
Qiu et al.

(10) Patent No.: US 10,765,825 B2
(45) Date of Patent: Sep. 8, 2020

(54) ENDOTRACHEAL TUBE DRAINAGE SYSTEM AND METHODS

(71) Applicant: CORESTONE BIOSCIENCES (BEIJING) CO., LTD., Beijing (CN)

(72) Inventors: Chunyuan Qiu, Huntington Beach, CA (US); Weiping Yang, Henderson, NV (US); Fei Cao, Beijing (CN); Bing Xu, Beijing (CN)

(73) Assignee: CORESTONE BIOSCIENCES (BEIJING) CO., LTD., Beijing (CN)

( * ) Notice: Subject to any disclaimer, the term of this patent is extended or adjusted under 35 U.S.C. 154(b) by 348 days.

(21) Appl. No.: 15/692,813

(22) Filed: Aug. 31, 2017

(65) Prior Publication Data

US 2019/0060594 A1 Feb. 28, 2019

(51) Int. Cl.
*A61M 16/04* (2006.01)

(52) U.S. Cl.
CPC .... *A61M 16/0434* (2013.01); *A61M 16/0402* (2014.02); *A61M 16/0445* (2014.02); *A61M 16/0459* (2014.02); *A61M 16/0463* (2013.01); *A61M 16/0477* (2014.02); *A61M 16/0479* (2014.02); *A61M 16/0486* (2014.02)

(58) Field of Classification Search
CPC .......... A61M 16/0434; A61M 16/0445; A61M 16/0479; A61M 16/0477; A61M 16/0459; A61M 16/0486; A61M 16/0463; A61M 16/0402; A61M 16/04; A61M 16/0454; A61M 16/0481; A61M 25/10; A61M 25/1002; A61M 25/1004; A61M 25/1025; A61M 25/1011; A61M 25/1009; A61M 25/1006; A61M 2025/105; A61M 2025/109; A61J 15/003–004

See application file for complete search history.

(56) References Cited

U.S. PATENT DOCUMENTS

| | | | |
|---|---|---|---|
| 3,810,474 A | 5/1974 | Cross | |
| 4,091,816 A | 5/1978 | Elam | |
| 4,328,056 A | 5/1982 | Snooks | |
| 4,340,046 A * | 7/1982 | Cox | A61M 16/04 128/200.26 |
| 4,423,725 A | 1/1984 | Baran et al. | |
| 4,693,243 A * | 9/1987 | Buras | A61M 16/04 128/207.15 |
| 5,033,466 A | 7/1991 | Weymuller, Jr. | |
| 5,765,559 A | 6/1998 | Kim | |

(Continued)

FOREIGN PATENT DOCUMENTS

| | | |
|---|---|---|
| EP | 0884061 A2 | 12/1998 |
| WO | 2012087837 A1 | 6/2012 |
| WO | 2015013380 A1 | 1/2015 |

*Primary Examiner* — Kendra D Carter
*Assistant Examiner* — Thao Tran
(74) *Attorney, Agent, or Firm* — McCoy Russell LLP

(57) ABSTRACT

An endotracheal tube (ETT) system and methods are provided. In at least one example, an ETT system may comprise, a tube, inflatable cuff coupled to the tube, and a restrictor. In at least one example the restrictor may comprise one more cavities. In a further example, a restrictor drainage assembly may be coupled to the restrictor, the restrictor drainage assembly configured to drain secretions that may be collected at a collection point formed by the restrictor when the ETT system is positioned in an airway of a patient and in an inflated state.

15 Claims, 8 Drawing Sheets

FIG. 4B

(56) References Cited

U.S. PATENT DOCUMENTS

| | | | |
|---|---|---|---|
| 5,830,184 A * | 11/1998 | Basta | A61M 25/00 604/104 |
| 8,196,584 B2 | 6/2012 | Maguire et al. | |
| 8,636,010 B2 | 1/2014 | Nelson et al. | |
| 8,733,359 B2 | 5/2014 | Schnell et al. | |
| 9,010,333 B2 | 4/2015 | Coates | |
| 2002/0014238 A1* | 2/2002 | Kotmel | A61M 16/04 128/204.18 |
| 2008/0021386 A1* | 1/2008 | Clayton | A61M 16/04 604/104 |
| 2008/0078401 A1 | 4/2008 | O'Neil et al. | |
| 2009/0032027 A1 | 2/2009 | McCachren et al. | |
| 2009/0107510 A1 | 4/2009 | Cornish et al. | |
| 2010/0262094 A1* | 10/2010 | Walton | A61M 1/0023 604/319 |
| 2013/0047992 A1 | 2/2013 | Kim et al. | |
| 2013/0160771 A1* | 6/2013 | Suijs | A61M 16/0475 128/207.15 |
| 2015/0101612 A1* | 4/2015 | Wang | A61M 16/0481 128/207.15 |
| 2017/0239434 A1* | 8/2017 | Bateman | A61M 16/044 |
| 2019/0105472 A1* | 4/2019 | Sharaiha | A61J 15/0003 |

\* cited by examiner

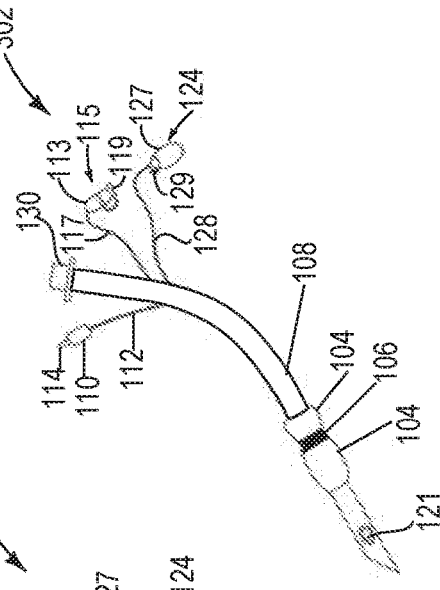
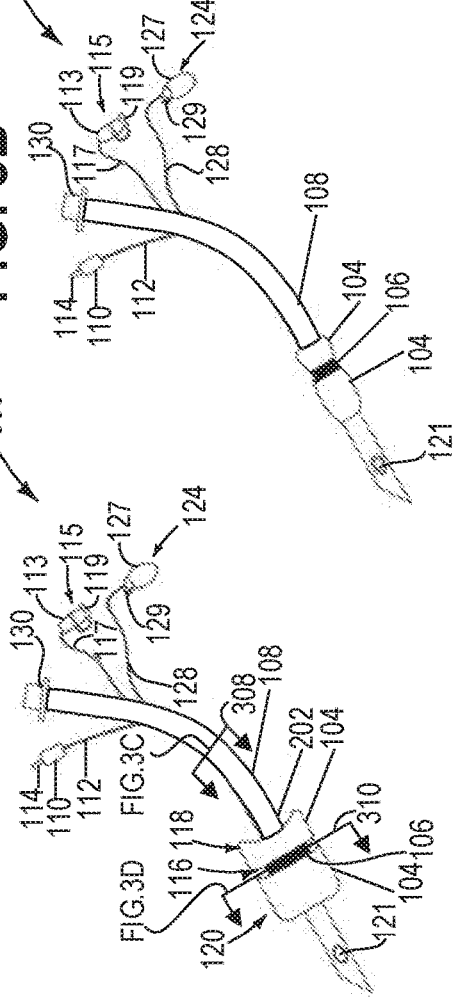
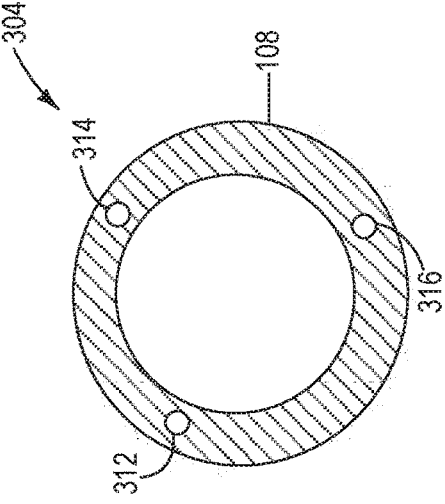
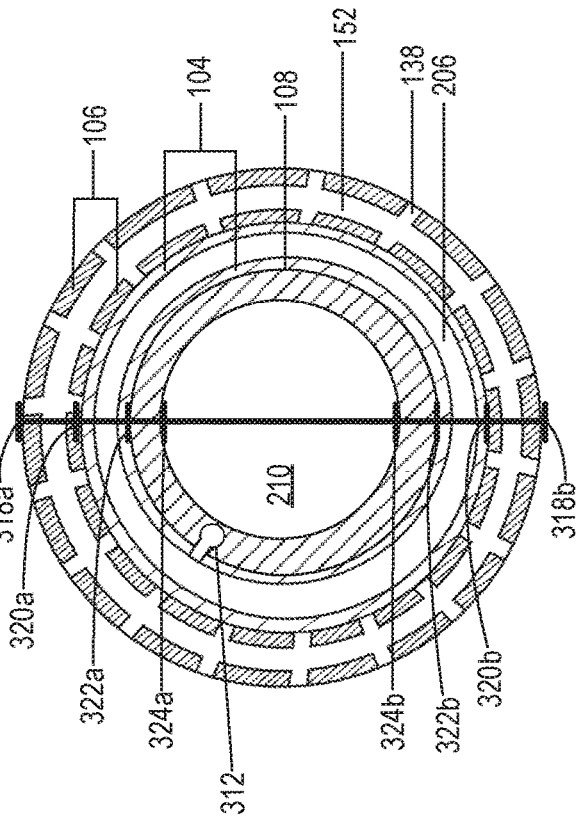

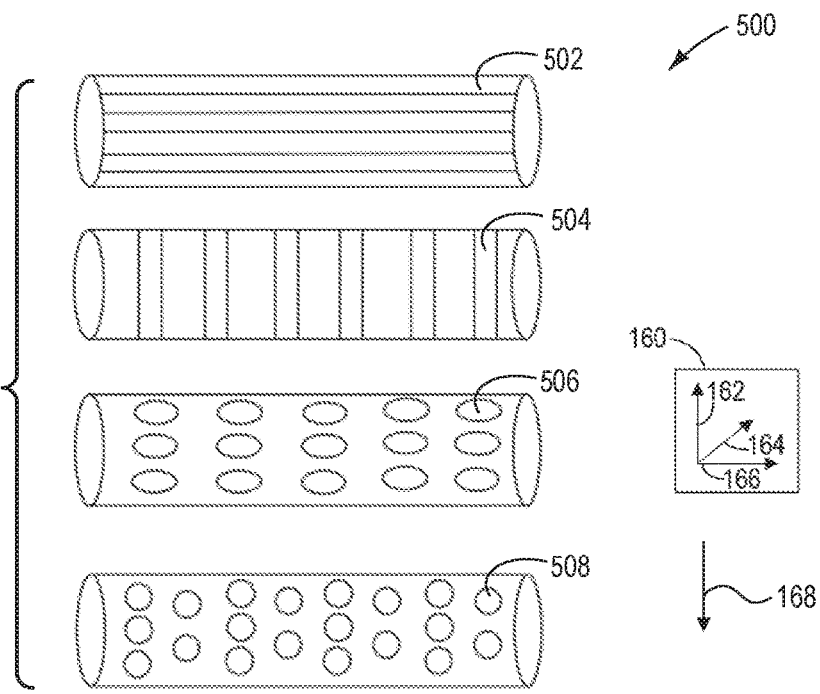
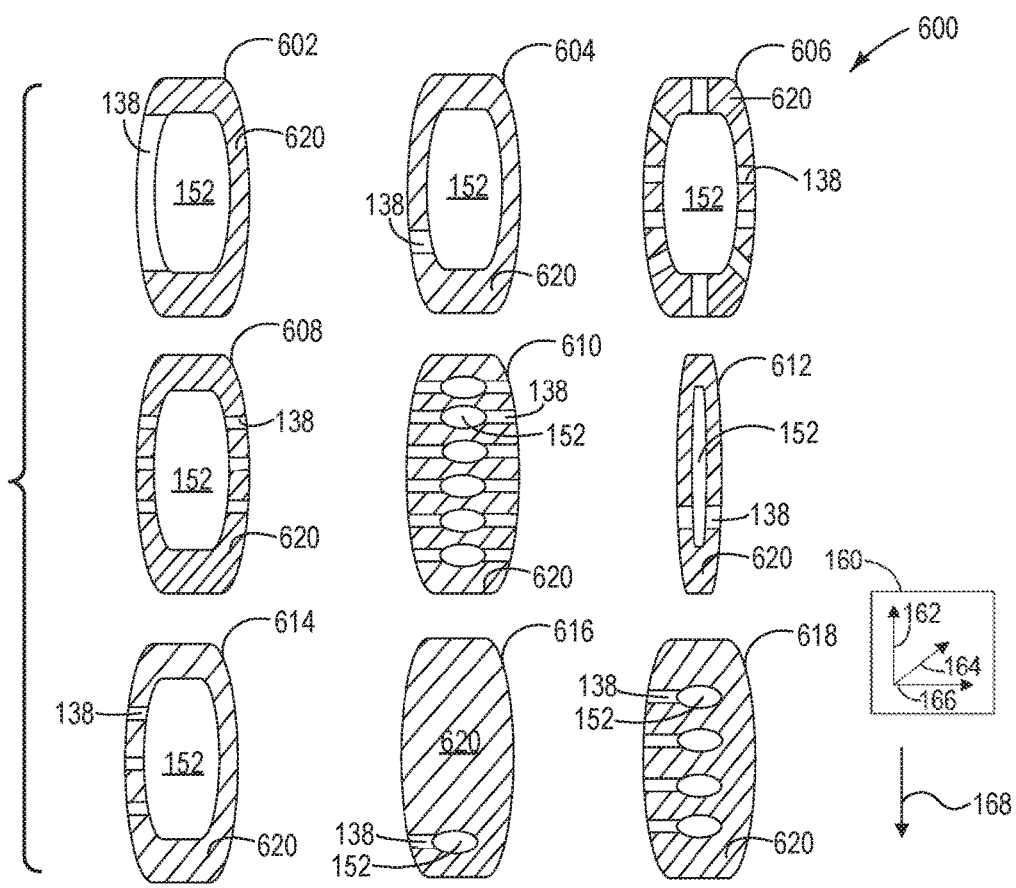

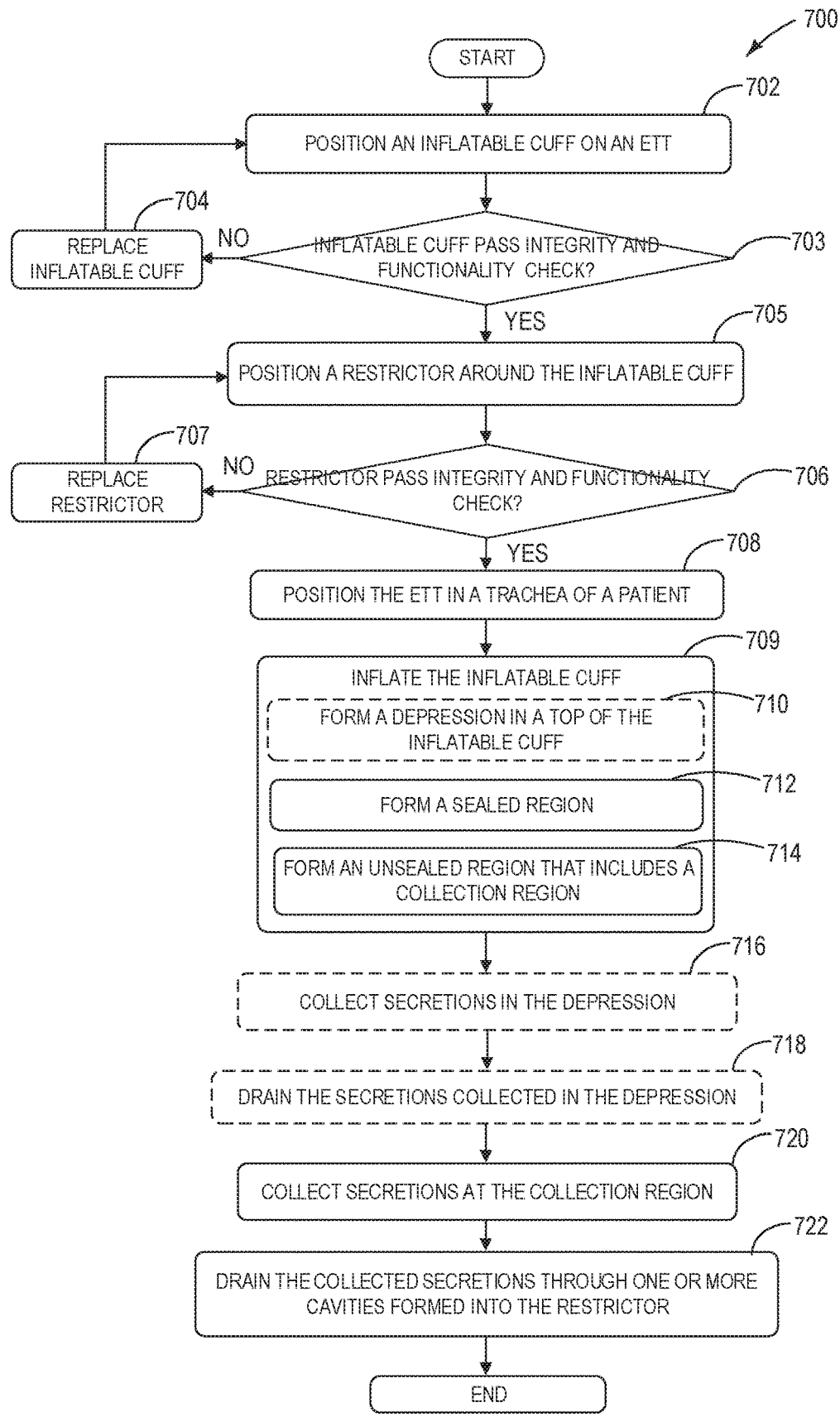

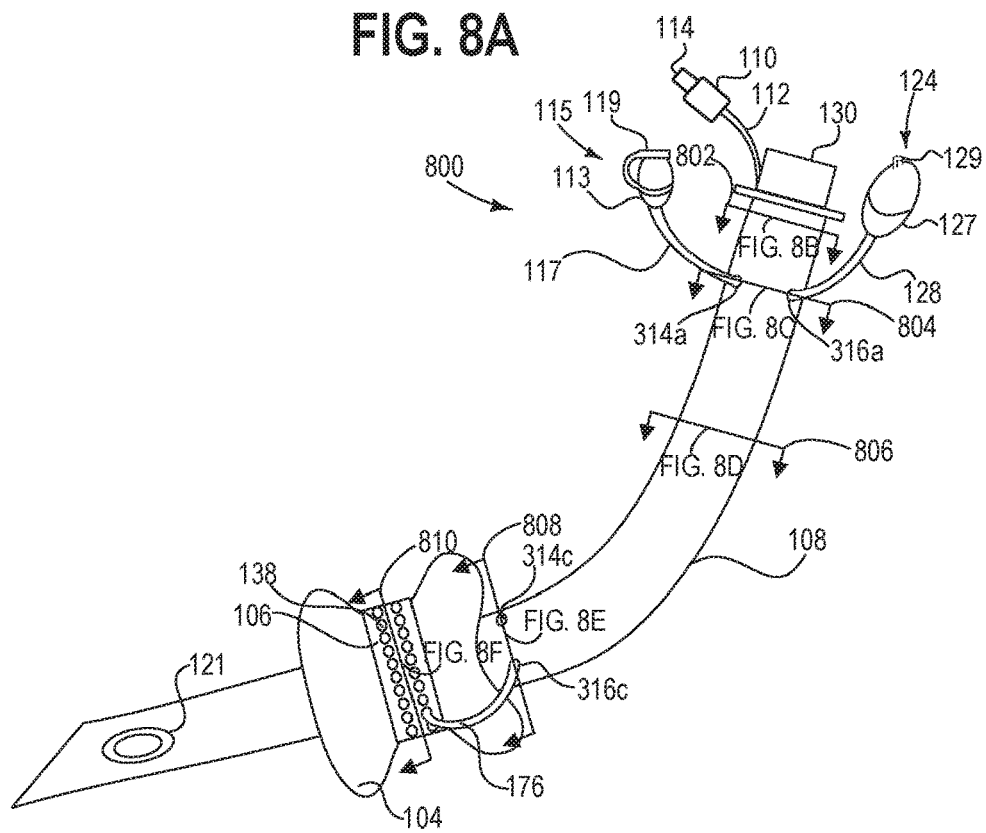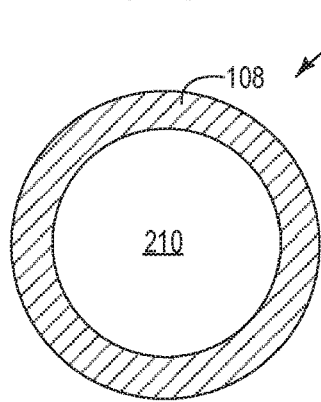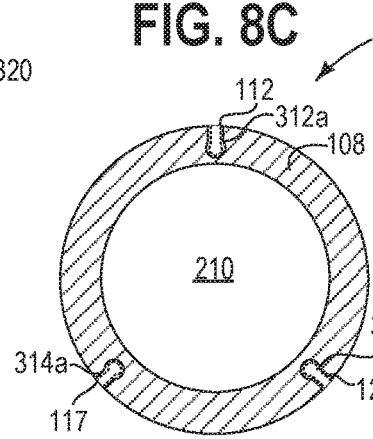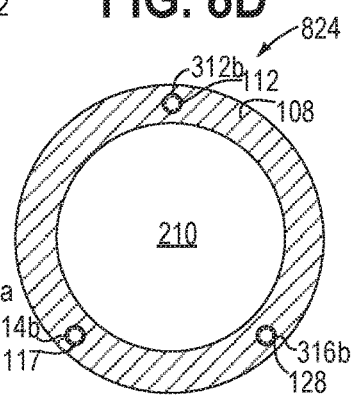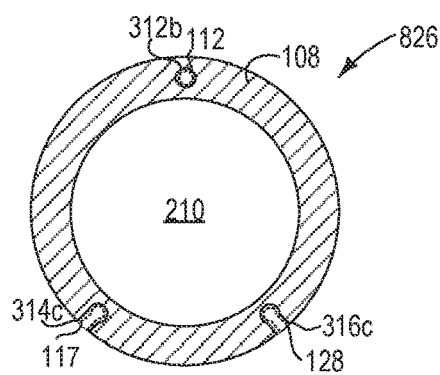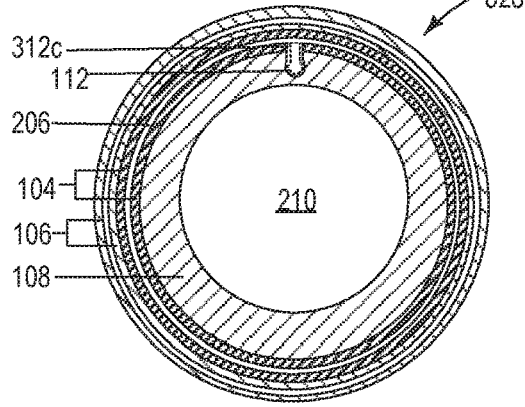

ENDOTRACHEAL TUBE DRAINAGE SYSTEM AND METHODS

BACKGROUND/SUMMARY

An airway tube system, such as an endotracheal tube (ETT) system, may include an inflatable cuff around an ETT of the ETT system for positioning the ETT in an airway of a patient and sealing the airway of the patient. For example, when the ETT is positioned in a patient, the inflatable cuff may be inflated to contact the airway wall of the patient in order to form a seal with the airway of the patient. This seal formed between the airway wall of the patient and the inflatable cuff may be beneficial for preventing aspiration, such as macroaspiration and microaspiration, of secretions of the intubated and ventilated patients, in at least one example. It is noted that reference to secretions herein may refer to bodily fluids of a patient, such sputum or mucus, for example. Additionally, sealing the airway of the patient may help to prevent objects foreign to the body of the patient from traveling down the airway of the patient.

However, it is very difficult to obtain a complete seal between the inflatable cuff and the airway wall of a patient, and in such examples where the inflatable cuff and the airway wall of the patient are not completely sealed, secretions of intubated and ventilated patients may accumulate upstream the inflatable cuff and leak downsntream the inflatable cuff and into a bronchial tree and lungs of the patient. The leakage of secretions into the bronchial tree and lungs may then potentially lead to undesirable biofilm formation, and, in some cases, develop into ventilation-associated pneumonia (VAP).

Specifically in a case of an ETT system, the shaping of many inflatable cuffs may be too round to form sufficient sealing with the trachea to prevent leakage of secretions past an inflatable cuff of the ETT system, as the trachea varies in shape from top to bottom. Further, the trachea varies in deformability from an anterior wall of the trachea that has cartilage to a posterior wall of the trachea comprising soft tissue posing further challenges to forming sufficient sealing between the inflatable cuff and the trachea. Thus, secretions may leak past the inflatable cuff via regions between the inflatable cuff and the trachea wall and into the bronchial tree and lungs of the patient due to the trachea wall variation in shape and rigidity preventing the inflatable cuff from forming a sufficient seal.

Previous approaches to address the above problems may have included varying a shape of the cuff to better seal the airway and collect the secretions. For example, previous approaches may have included attaching reinforcement material on an inside of the cuff to restrict a portion of the cuff for shaping purposes. Further, previous approaches may have also included molding the inflatable cuff, so that the inflatable cuff includes one or more restricted portions upon inflation of the inflatable cuff.

Additionally, other previous approaches may have included the use of multiple cuffs to form multiple seals between the ETT system and the airway of the patient, such as taught in US 2009/0032027 A1. Thus, secretions which may leak past a first cuff may be trapped between the first cuff and a second cuff, rather than the secretions draining into a bronchial tree and lungs of a patient.

However, the inventors have recognized several problems with the above approaches. For example, approaches that include attachment of reinforcement material to an interior of an inflatable cuff to shape the inflatable cuff, that mold the inflatable cuff to include one or more restricted portions, and that use a plurality of separate cuffs to improve sealing of the airway may be complex to produce. Further, as these approaches for shaping the inflatable cuff are complex to produce, a number of valleys and a positioning of the valleys may be difficult to alter in a case where patient require such adjustments to prevent aspiration of secretions during intubation. Moreover, these previous approaches fail to include robust drainage systems to remove trapped secretions.

Thus, recognizing the above problems, the inventors herein have developed an ETT system for collecting and draining secretions, so that aspiration of such secretions may be prevented. Additionally, the ETT system developed by the inventors may prevent aspiration of foreign objects, such as debris that may enter the airway while a patient is intubated, for example.

In at least one example, the ETT system developed by the inventors includes an inflatable cuff surrounding a tube (i.e., ETT), and a restrictor including one or more cavities, the restrictor surrounding an outer surface of the inflatable cuff, such that the inflatable cuff is positioned between the restrictor and the tube. The restrictor may restrict the inflatable cuff to form a valley region of the inflatable cuff that positioned between protruding regions of the inflatable cuff when the inflatable cuff is in an inflated state, and a drainage assembly may be coupled to the restrictor in at least one example.

The above ETT system developed by the inventors achieves several advantages. For example, when the above described ETT of the ETT system is positioned in a trachea of a patient and in the inflated state, the protruding regions of the inflatable cuff may contact the trachea wall of the patient to form at least upper and lower seal segments, while the valley formed between the protruding regions may not contact the trachea wall of the patient. Put another way, the protruding regions of the inflatable cuff may form sealed regions with the trachea wall of the patient, while the valley of the inflatable cuff may form an unsealed region with the trachea wall of the patient, where a sealed region is a region of contact between the trachea wall of the patient and the inflatable cuff. An unsealed region positioned between two sealed regions of the ETT system when the ETT system is in the inflated state and positioned in a patient enables collection of secretions at the unsealed region. The secretions collected at the collection region formed at the unsealed region may then be drained via suction of the collected secretions through the one or more cavities formed into the restrictor via a drainage bulb coupled to the restrictor.

For example, the secretions collected at the collection region may be removed via a restrictor drainage assembly that utilizes active suctioning of the collected secretions to move the collected secretions through one or more cavities formed in the restrictor, through a restrictor drainage line, and into a collection reservoir of a restrictor drainage bulb.

Thus, the above approach developed by the inventors may better prevent aspiration compared to traditional approaches, as the above approach may both collect and drain secretions in a robust manner. Benefits in regards to qualifying and sampling the collected secretions for laboratory studies may also be realized. Furthermore, the drainage bulb suction pressure applied to the unsealed region that is positioned between the sealed regions advantageously enables monitoring of a quality of both the upper and lower balloon seals. Thus, potential balloon malfunctions following placement of the ETT system in a patient may be detected and addressed. Moreover, the simplicity of the ETT system developed by the inventors may reduce a cost for manufacturing the ETT system compared to previous approaches.

BRIEF DESCRIPTION OF THE FIGURES

FIG. 3A shows a view of a second example ETT system in an inflated state according to at least one example of the present disclosure.

FIG. 3B shows a view of the second example ETT system in a deflated state according to at least one example of the present disclosure.

FIG. 3C shows a first cross-sectional view of the second example ETT system according to at least one example of the present disclosure.

FIG. 3D shows a second cross-sectional view of the second example ETT system according to at least one example of the present disclosure.

FIG. 5 shows example cavity configurations for a restrictor according to at least one example of the present disclosure.

FIG. 6 shows example cross-sections of restrictors according to at least one example of the present disclosure.

FIG. 7 shows a flow chart of an example method according to at least one example of the present disclosure.

FIG. 8A shows a view of a fourth example ETT system according to at least one example of the present disclosure.

FIG. 8B shows a first cross-sectional view of the fourth example ETT system according to at least one example of the present disclosure.

FIG. 8C shows a second cross-sectional view the fourth example ETT system according to at least one example of the present disclosure.

FIG. 8D shows a third cross-sectional view of the fourth example ETT system according to at least one example of the present disclosure.

FIG. 8E shows a fourth cross-sectional view of the fourth example ETT system according to at least one example of the present disclosure.

FIG. 8F shows a fifth cross-sectional view of the fourth example ETT system according to at least one example of the present disclosure.

DETAILED DESCRIPTION

The following description relates to an ETT system including an inflatable cuff and a restrictor including one or more cavities coupled to an ETT of an ETT system. In at least one example, the restrictor may be coupled to an outer surface of the inflatable cuff. However, in other examples, the restrictor may be coupled directly to a tube (ETT) of the ETT system. In at least one example the restrictor may be a band. Thus, restrictor may also be referenced to as a band herein.

In examples where the restrictor may be positioned on the outer surface of the inflatable cuff, the restrictor may restrict the inflatable cuff and shape the inflatable cuff to have a valley that is positioned between protruding regions of the inflatable cuff. In examples where the restrictor may be coupled directly to a tube of the ETT system, the restrictor may be positioned between two separate inflatable cuffs of the ETT system, each of the inflatable cuffs forming a protruding region. Secretions may be collected between the two protruding regions of the ETT system (i.e., between protruding regions of the inflatable cuff or between the two separate inflatable cuffs of the ETT system). The collected secretions may then be suctioned through the one or more cavities formed into the restrictor to drain the secretions. Thus, aspiration of such secretions may be prevented.

Figure 1A:
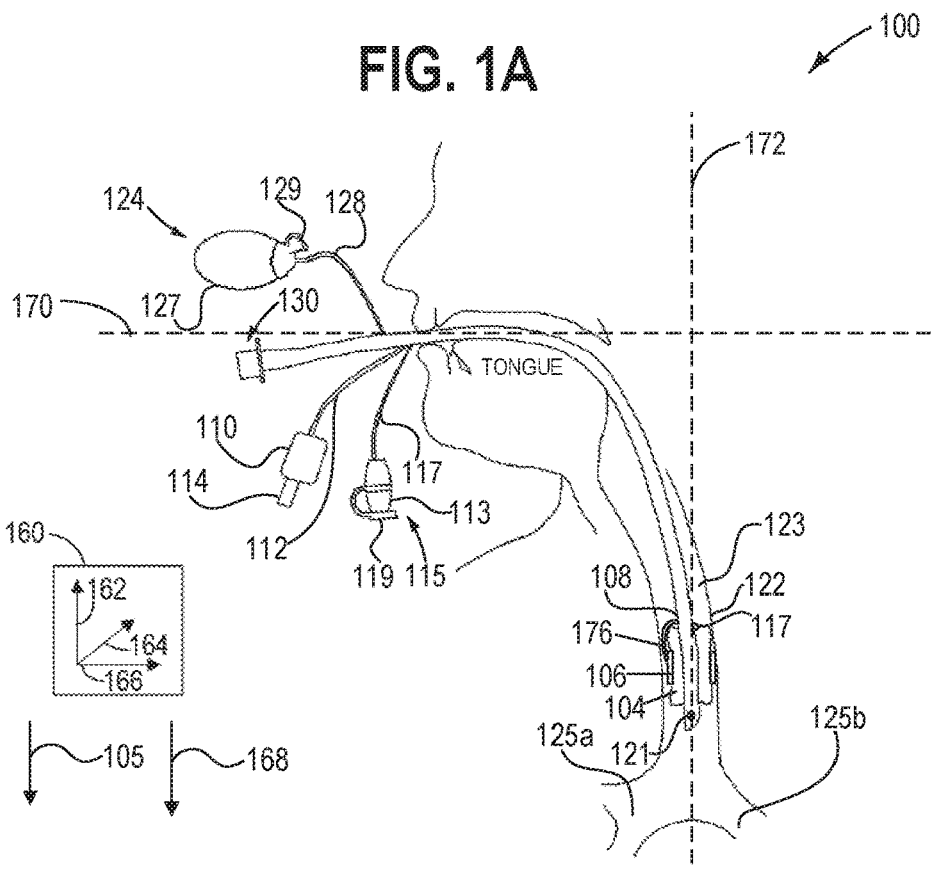
FIG. 1A shows a view of a first example ETT system in a deflated state and positioned in a patient according to at least one example of the present disclosure.
Figure 1B:
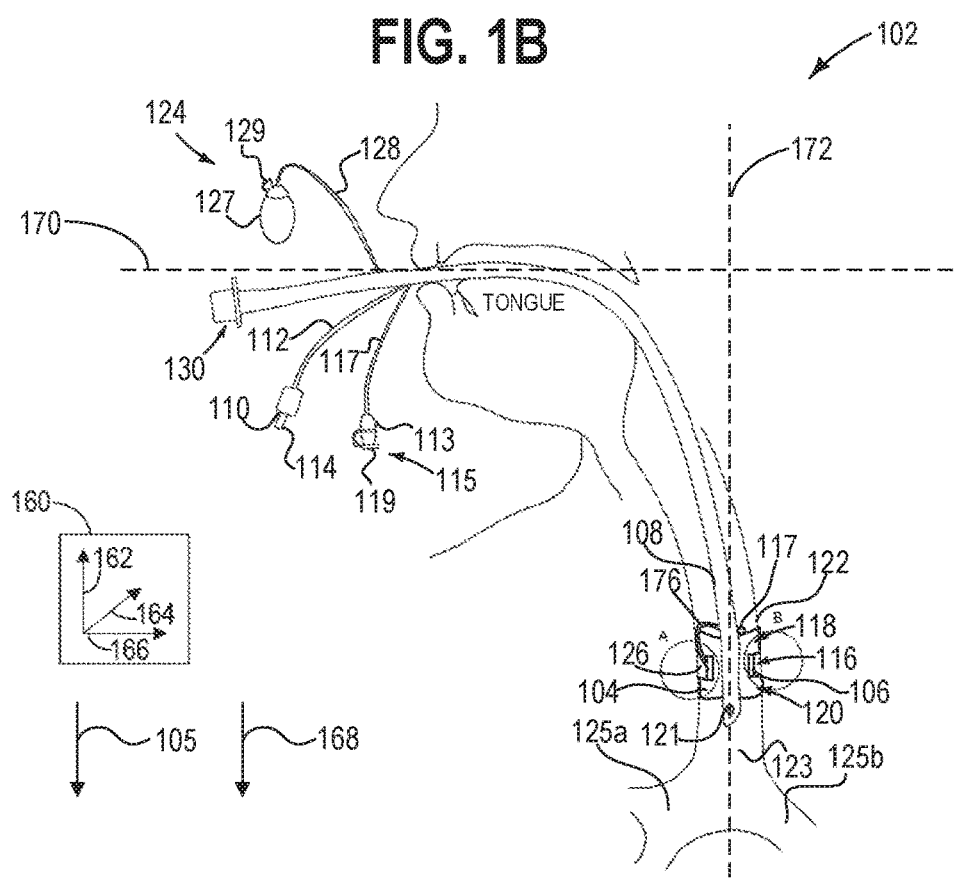
FIG. 1B shows a view of the first example ETT system in an inflated state and positioned in a patient according to at least one example of the present disclosure.

As shown in FIGS. 1A and 1B, the ETT is positioned in an airway of a patient in a deflated state, and once the inflatable cuff of the ETT system is inflated, the restrictor shapes the inflatable cuff such that two protruding regions of the inflatable cuff contacting a trachea wall of the patient to form sealed regions, while the valley of the inflatable cuff is recessed relative to the trachea wall of the patient and does not contact the trachea wall of the patient to form an unsealed region.

Figure 1C:
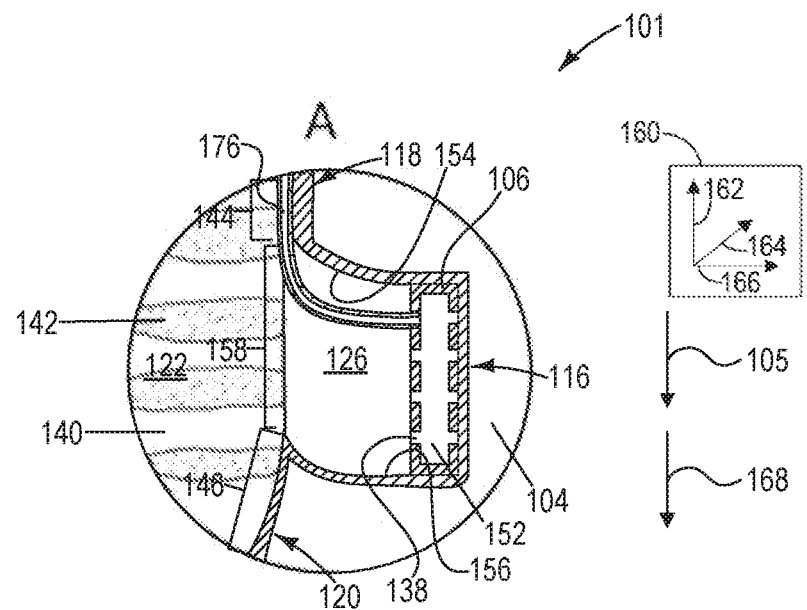
FIG. 1C shows an exploded cross-sectional view of a region of the first example ETT system in the inflated state and positioned in the patient.
Figure 1D:
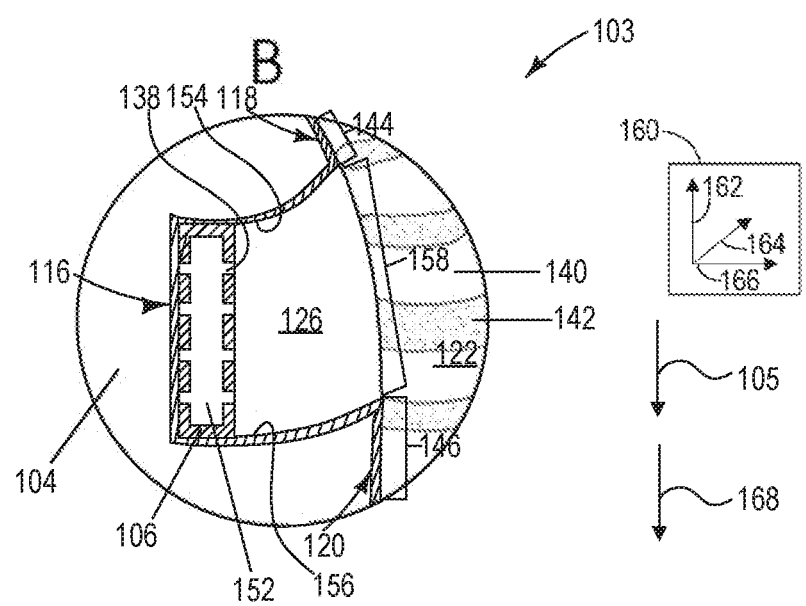
FIG. 1D shows a second exploded cross-sectional view of a second region of the first example ETT in the inflated state and positioned in the patient.
Figure 2:
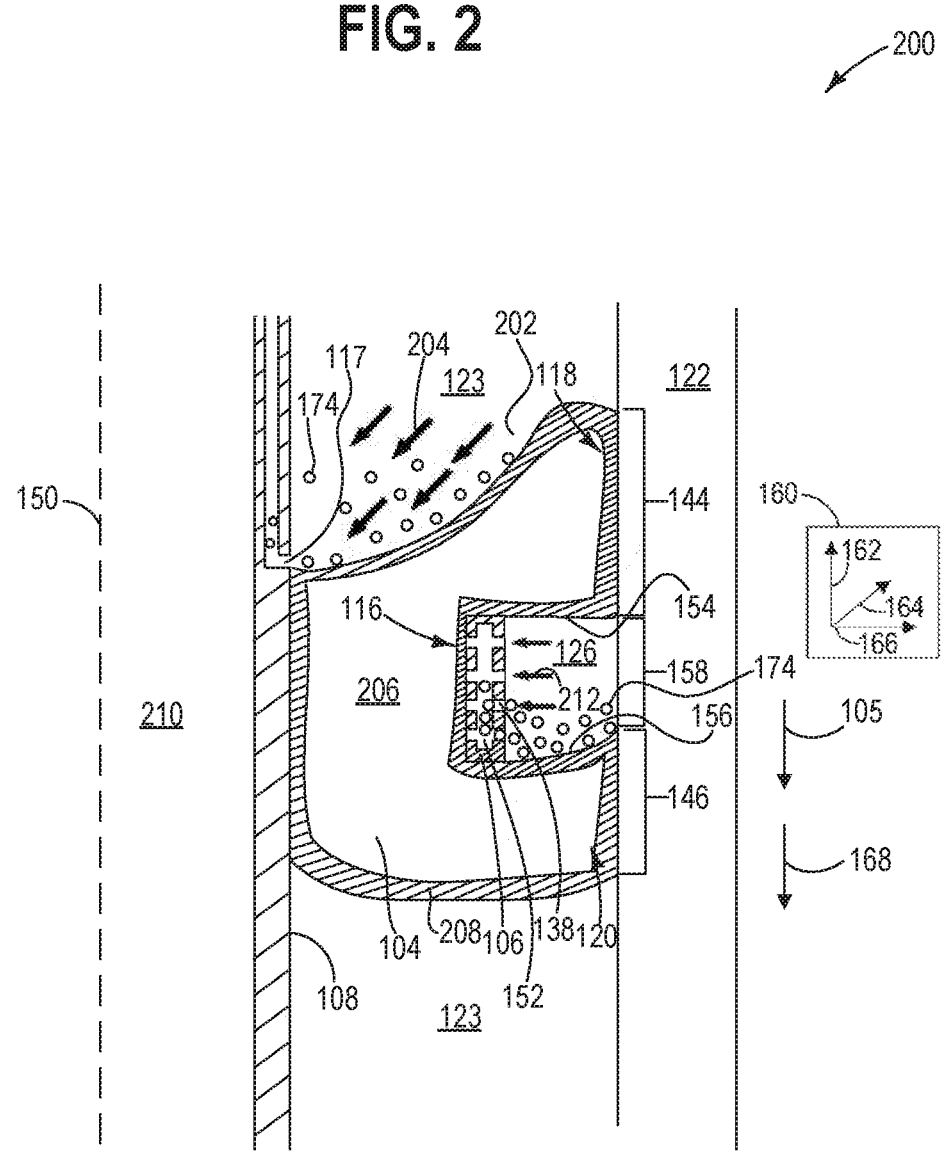
FIG. 2 shows a schematic representation of flow through an ETT system according to at least one example of the present disclosure.

The shaping of the inflatable cuff of the ETT system to include a valley recessed relative to the trachea wall of the patient between protruding regions of the inflatable cuff that contact the trachea wall may be advantageous, as secretions which may leak past a first protruding region that is positioned upstream of the valley and upstream of a second protruding region may be trapped between the valley and the trachea wall, as shown in FIGS. 1C-1D and in FIG. 2. Specifically, the secretions may be trapped between the restrictor forming the valley and the trachea wall.

Figure 4B:
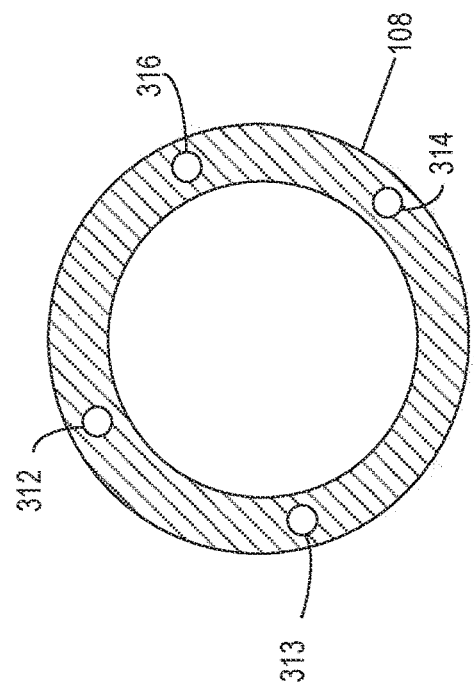
FIG. 4B shows a cross-sectional view of the third example ETT system according to at least one example of the present disclosure.
Figure 4A:
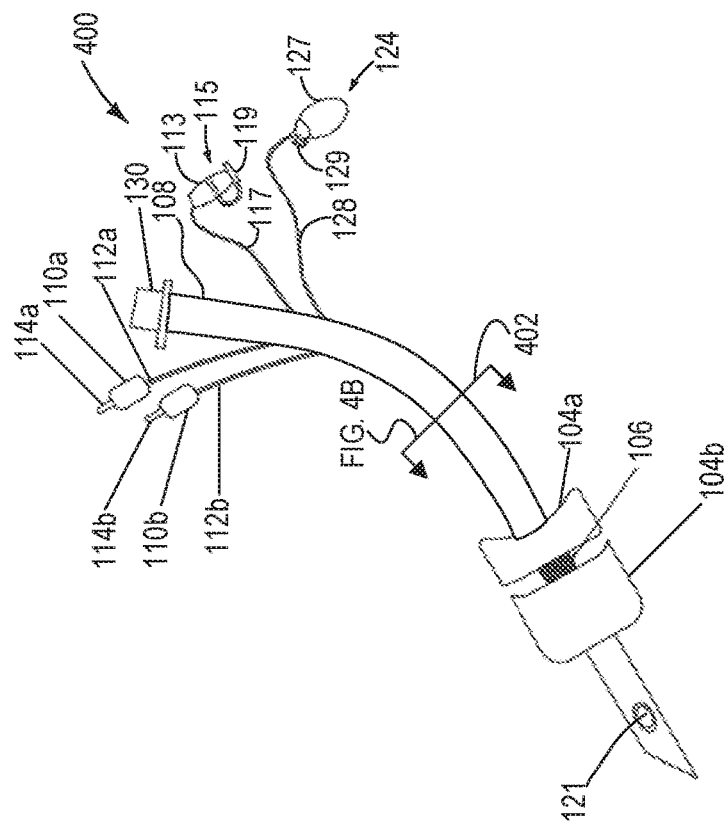
FIG. 4A shows a view of a third example ETT system comprising a plurality of inflatable cuffs according to at least one example of the present disclosure.

A similar shaping may be achieved via two separate inflatable cuffs, such as shown in FIG. 4A. In examples where the above described shaping is achieved via two separate inflatable cuffs, a restrictor may be positioned and surrounding a tube of an ETT system in a valley formed directly between two the separate inflatable cuffs when the inflatable cuffs are in the inflated state. Thus, rather than the restrictor restricting the inflatable cuff, the restrictor may be coupled directly to the elongated tube of the ETT system, where the restrictor is positioned between the two separate inflatable cuffs. In such examples that may include multiple separate cuffs, secretions that may leak downstream past a first, upstream inflatable cuff, may be trapped between the valley and the trachea wall, and the secretions may be trapped upstream of a second, downstream inflatable cuff, where the second inflatable cuff is separate from the first inflatable cuff. Specifically, the secretions may be trapped between the restrictor coupled to the tube of the ETT system at the valley formed between the separate inflatable cuffs and the trachea wall.

Thus, the second protruding region/second separate inflatable cuff may act as a back-up seal should any secretions leak past the first protruding region/first inflatable cuff to reduce the chances for the occurrence of aspiration, and the valley may act as a collection chamber.

Additionally, in at least one embodiment, more than one restrictor may be positioned on an outer surface of the inflatable cuff to create multiple valleys and/or more than two separate inflatable cuffs may be included to create multiple valleys. By creating multiple valleys, and thus multiple unsealed regions that are positioned directly between sealed regions when the ETT is positioned in a patient in an inflated state, the chances for aspiration to occur may be even further reduced.

The restrictor may include one or more cavities and the restrictor may be coupled to a drainage assembly. Thus, the restrictor advantageously provides a simple and robust drainage system for draining secretions collected via the disclosed ETT system.

As shown in FIGS. 3A-3D, in at least one example, the restrictor positioned on an outside of the inflatable cuff includes one or more cavities that communicate into an interior space of the restrictor to enable suction of secretions through the one or more cavities, through the interior space of the restrictor, through a restrictor drainage line that may be formed into the wall of the ETT, and into a collection reservoir of a drainage bulb, as discussed in FIG. 7.

Further, as also shown in FIGS. 3A-3D, ports may be formed into the ETT itself for the passage of fluids. For example, one or more of ports for the passage of air from atmosphere, where the ports are open to the atmosphere above the inflatable cuffs, may also open into the inflatable cuffs to inflate the inflatable cuffs. Additionally, ports for the passage of secretions when draining the secretions out of the airway may be formed into the wall of the ETT.

In embodiments where a restrictor includes one or more cavities for draining secretions that are collected via the ETT system, several configurations for the one or more cavities may be used, as shown at FIGS. 6-7.

FIGS. 1-7 are not drawn to scale and are provided for illustrative purposes. Further, FIGS. 1-7 show the relative positioning of various components of the receiver assembly. If shown directly contacting each other, or directly coupled, then such components may be referred to as directly contacting or directly coupled, respectively, at least in one example. Similarly, components shown contiguous or adjacent to one another may be contiguous or adjacent to each other, respectively, at least in one example. As an example, components lying in face-sharing contact with each other may be referred to as in face-sharing contact or physically contacting one another. As another example, elements positioned apart from each other with only a space therebetween and no other components may be referred to as such, in at least one example.

As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example. Additionally, the terms upstream and downstream in the present disclosure are defined based on a direction of air flow during inhalation. For example, during inhalation air flows in a direction from atmosphere and into the lungs of a patient via an airway of the patient. Thus, as upstream and downstream are defined based on a direction of air flow during inhalation, a mouth of the patient is upstream a trachea of the patient, and the trachea of the patient is upstream the bronchi of the patient.

For purposes of discussion, the following will be described collectively. Thus, elements introduced in a first figure may not be reintroduced in later figures, and these repeated elements may be numbered similarly.

FIG. 1A shows a cross-sectional view of a first example ETT system 100 in a deflated state according to an example of the present disclosure, where the ETT system 100 in the deflated state is positioned in a patient. The ETT system 100 in the deflated state refers to a condition where the inflatable cuff 104 of the ETT system 100 is in a deflated state. That is, the deflated state may be a state where the inflatable cuff 104 is flat and not expanded due to lack of air trapped in the inflatable cuff.

An axis system 160 comprising three axes, namely an x-axis 166 parallel to a horizontal direction, a y-axis 162 parallel to a vertical direction, and a z-axis 164 perpendicular to both the x- and y-axes is shown. Each of x-axis 166, y-axis 162, and z-axis are positive in a same direction as the arrows point for each of the x-axis 166, y-axis 162, and z-axis are pointing. Further, each of x-axis 166, y-axis 162, and z-axis 164 are negative in a direction opposite the direction the arrows point for each of x-axis 166, y-axis 162, and z-axis 164. A direction of gravity 168 is shown extending parallel to the negative y-axis direction. Further, a general direction of airflow during inhalation at a trachea 123 of the patient 105 is shown for reference.

The ETT system 100 comprises an elongated tube 108 (also referred to herein as an ETT), and an inflatable cuff 104 positioned on an exterior surface of the wall of tube 108. Tube 108 may also be referred to as the ETT herein. Air may be flowed through tube 108 of the ETT system into the bronchi 125a, 125b, and further into the lungs of the patient (not shown) during inhalation. Further, during exhalation, air may also be flowed in the reverse direction through tube 108. Tube 108 may be gradually bent in shape in order to match the bend of an airway of a patient. It is noted that air from flowed through the tube 108 may be air that is external to a body of the patient. For example, the air may be introduced via a ventilator, or the air that may be introduced from an environment immediately external to a body of the patient.

An axis 170 that is parallel to x-axis 166 is shown intersecting with an axis 172 that is parallel to y-axis 162. When ETT system 100 is positioned in the patient, as shown in FIG. 1A, tube 108 of ETT system 100 is shaped to be approximately parallel to axis 170 at a mouth of a patient (above a tongue of the patient), and tube 108 gradually bends when downstream of the tongue of the patient until the tube 108 is substantially parallel to axis 172 at a trachea 123 of the patient. Thus, tube 108 bends such that a portion of the tube 108 that is upstream the tongue or at a tongue of a patient substantially horizontal and such that a portion of the tube that is downstream the tongue is substantially vertical. In particular, a portion of the tube 108 that is positioned in a trachea of the patient may be substantially vertical. In some embodiments, to accommodate such bending, tube 108 may comprise a flexible material. In other examples the tube 108 may be pre-formed to the bent shape, however.

In at least one example, the inflatable cuff 104 completely surrounds the exterior surface, also referred to herein as an outer surface, of the tube 108 for a portion of a length of the elongated tube 108. Thus, the inflatable cuff 104 does not surround the exterior surface of the tube 108 for an entire length of the elongated tube 108 of ETT system 100. Instead, the inflatable cuff 104 only surrounds the exterior surface of the wall of tube 108 for a portion of the length of the ETT system 100. The portion of the length of the ETT system 100 surrounded by the inflatable cuff 104 may be near an end of the elongated tube that is most downstream when the ETT system 100 is positioned in the patient, for example.

At least one sealed region may be formed between the inflatable cuff 104 trachea wall 122 to prevent leakage downstream of the inflatable cuff 104. Thus, air and other secretions may be prevented from flowing through the airway of the patient outside of tube 108 downstream of the inflatable cuff 104 due to a seal formed between the trachea wall 122 and the inflatable cuff 104, while air may flow through the tube 108 as described above.

Additionally, the inflatable cuff 104 of the present disclosure may be shaped in a manner to prevent aspiration of secretions. Specifically, the inflatable cuff 104 may be shaped to form one or more collection regions as well as one or more seal segments that collect secretions of the patient and prevent these secretions from being aspirated by the patient.

The inflatable cuff 104 may be shaped to form a collection region via a restrictor 106, for example. It is noted that restrictor 106 is shown for illustrative purposes in FIGS. 1A and 1B to show a positioning of the restrictor 106. Further details regarding the features of restrictor 106 may be found in the remaining figures.

Restrictor 106 may be positioned on an exterior surface of the inflatable cuff 104, encircling the inflatable cuff 104. In at least one example, the restrictor 106 may comprise a soft, flexible material to be gentle on the trachea wall during intubation and extubation of a patient. For example, the restrictor 106 may comprise one or more of silicon, PVC, and polyurethane. In at least one example, the restrictor 106 may form a loop, and the restrictor 106 may surround the exterior surface of the inflatable cuff 104 360°. In particular, the restrictor 106 may surround the exterior surface of the inflatable cuff 104, such that at least a portion of the exterior surface of the inflatable cuff 104 is in contact with the restrictor 106. In some examples, the restrictor 106 may be a single, unitary piece. Furthermore, in at least one embodiment, the restrictor 106 may be a band. However, other restrictors may be possible. For example, in some embodiments the restrictor may be a clamp. In at least one embodiment, the restrictor 106 may be fixed to the inflatable cuff 104 such that the restrictor 106 may be un-movable. By fixing the restrictor 106 to the inflatable cuff 104 in an un-movable manner, proper positioning of the restrictor 106 to the inflatable cuff 104 may be maintained during a positioning of the ETT in the patient. However, in other examples the restrictor may be movably coupled to the inflatable cuff 104 to enable easy alteration of valley positioning (and thus a position of a collection region), for example. Furthermore, the shape, size and location of the restrictor can determine the shape, size and location of both the valley and the cuff, the later will further determine the seal points and segments of the cuff and trachea.

Furthermore, in at least one example, an ETT system may comprise a plurality of restrictors that at least partially surround a same inflatable cuff, where some of the plurality of restrictors may be movably coupled to the inflatable cuff 104 and a remainder of the plurality of restrictors may be fixed to the inflatable cuff 104 and not movable. Thus, in such examples, the inflatable cuff may be shaped in a manner that properly seals in the airway of most patients via one or more restrictors that are un-movably fixed to the inflatable cuff 104, and one or more restrictors may optionally be movably coupled to the inflatable cuff 104 to alter the shaping of the inflatable cuff 104 in a case where the shaping via the fixed restrictor(s) does not fit an airway for a particular patient to properly seal.

The portion of the restrictor 106 that may be in contact with the exterior surface of the inflatable cuff 104 may be an inner circumference of the restrictor 106. For example, in at least one embodiment where the restrictor 106 is a band, the band may form a complete loop, where the band includes both an inner circumference and an outer circumference. The inner circumference of the band may be a circumference that is surrounded by an exterior surface of the band. The outer circumference of the band may be an outermost circumference of an exterior of the band.

Further, in examples where the restrictor 106 is a band, an inner diameter of the band may be approximately a same or smaller diameter as an outermost diameter of the inflatable cuff 104 when the inflatable cuff 104 is in the deflated state. When the inflatable cuff 104 is transitioned to an inflated state, the band may restrict a portion of the inflatable cuff 104 that is in contact with the band from expanding, as is discussed below in reference to FIG. 1B.

The restrictor 106 may be in direct contact with the exterior surface of the inflatable cuff 104 in at least one example. In examples where the restrictor 106 may be in direct contact with the inflatable cuff 104, the restrictor 106 may be coupled to the inflatable via only frictional forces. Additionally or alternatively, an adhesive or anchor mechanism may be used to couple the restrictor 106 to the inflatable cuff 104. Thus, in such examples, the restrictor 106 may not be in direct contact with the exterior surface of the inflatable cuff 104, and the restrictor 106 may instead be separated from the exterior wall of tube 108 by a layer of adhesive.

In at least one example, a portion of the restrictor 106 may be in direct contact with the exterior surface of the inflatable cuff 104, while a remaining portion of the restrictor 106 may contact an adhesive that is in contact with the exterior surface inflatable cuff 104. Thus, in such examples, a combination of frictional forces between the restrictor 106 and the exterior surface of the wall of tube 108 as well as an adhesive may couple the restrictor 106 to the exterior surface of the inflatable cuff 104.

Additionally or alternatively, a restrictor 106 may include a tail 176 that connects to restrictor drainage line 128. The tail 176 may connect to the restrictor drainage line 128 at an end opposite an end of the restrictor drainage line 128 that is connected to the restrictor drainage bulb 124. For example, the restrictor drainage line 128 may be positioned in a port formed into a wall of the ETT 108, and the tail 176 of the restrictor 106 may connect to the end of the restrictor drainage line 128 that is opposite the end of the restrictor drainage line 128 connected to the restrictor drainage bulb 124.

Alternatively, in some examples, the restrictor drainage line 128 may be formed in part by a port integral with the wall 108 of the ETT, and the tail 176 of the restrictor 106 may connect either directly with the restrictor drainage line port or connect with a portion of the restrictor drainage line 128 that is connected to the restrictor drainage line port proximal the inflatable cuff 104.

In at least one example, the tail 176 of the restrictor 106 may be integral with the restrictor 106, and the tail 176 of the restrictor 106 may be a hollow tail that opens into the interior space of the restrictor 106. Such examples where the tail 176 is integral with the restrictor 106 may be advantageous for simplifying assembly of the ETT system. Alternatively, the tail 176 may be a separate tube that connects the restrictor 106 to the wall of ETT 108. For example, a first end of the tail 176 may be connected to the restrictor 106 via an opening formed into the restrictor 106, and a second end of the tail 176 opposite the first end of the tail 176 may be connected to an opening formed into the ETT 108, such as a restrictor drainage line port that is formed into the ETT 108. Examples where the tail 176 is formed as a separate piece may be advantageous for maintenance of the ETT system. For example, the tail 176 being formed as a separate piece may be advantageous for addressing degradation issues that may occur at the tail 176, as the tail 176 may simply be replaced as opposed to having to replace the entire restrictor 106.

Thus, the tail 176 of the restrictor 106 may anchor the restrictor band to the ETT, as well as form part of a suctioning passageway to enable secretions to be suctioned through the restrictor 106 and into the restrictor drainage bulb 124. Further details regarding the tail 176 of the restrictor 106 are discussed later herein.

The shape, size and location of the restrictor 106 can determine the shape, size, and location of both the valley and determines the seal points and segments between the inflatable cuff 104 and the trachea wall 122.

In at least one embodiment, the restrictor 106 itself may be hollow. In this case, the restrictor that covers 0-360-degree circumference functions as a fluid collection site or temporary reservoir. For example, the restrictor 106 may be a band that is tubular in shape with an interior space formed therein in at least one embodiment. The lumen formed within the restrictor 106, such as a band, may be continuous in at least one example. In such examples where the restrictor 106 may be hollow, the restrictor 106 may include one or more cavities that open through a wall of the restrictor 106 and into the hollow interior space of the band 106. The one or more cavities may be particularly beneficial for enabling active drainage of secretions collected at a collection region formed by the inflatable cuff through the restrictor, as will be explained in further detail below.

In at least one example, the ETT system 100 that is in the deflated state may be advantageous for positioning the ETT system 100 in an airway of the patient during intubation. For example, the smaller diameter of the inflatable cuff 104 while the inflatable cuff 104 is in the deflated state as opposed to when the inflatable cuff 104 is in the inflated state may make it easier to move the ETT system 100 through an airway of a patient. As such, the ETT system 100 in the deflated state may be easier to position in a desired location of the patient than the ETT system 100 in an inflated state, as a diameter of the inflatable cuff 104 is smaller for an ETT system 100 that is in the deflated state than a diameter of the inflatable cuff 104 when the ETT system 100 is in the inflated state (i.e., when inflatable cuff 104 is filled with air).

In at least one example, the ETT system 100 in the deflated state may be positioned such that the inflatable cuff 104 of the ETT system 100 is located in the trachea 123 of the patient, upstream of bronchi 125a, 125b of the patient. Once the ETT system 100 in the deflated state is positioned in a desired location of the patient's airway, the inflatable cuff 104 may be inflated to transition the ETT system 100 to be in an inflated state. The ETT system in the inflated state, as shown in FIG. 1B, may hold the ETT system in position, as the inflatable cuff 104 may increase in diameter and push against the trachea wall 122 of the trachea 123 of the patient when in the inflated state. Additionally, multiple sealing regions may be formed between the inflatable cuff 104 and the trachea wall 122 when the ETT system is in the inflated state.

In at least one example, the inflatable cuff 104 may be inflated via an inflation assembly. In at least one example, the inflation assembly may comprise a pilot balloon, a one-way valve 114 coupled to the pilot balloon 110, and a pilot line 112 coupling the pilot balloon 110 to the inflatable cuff 104. In particular, in order to inflate the inflatable cuff 104, air may be introduced into the inflatable cuff 104 by flowing air through the one-way valve 114, through the pilot balloon 110, through the pilot line 112, and into the inflatable cuff 104. For example, air may be injected through the one-way valve 114 and into the pilot balloon 110 via a syringe to inflate the inflatable cuff 104.

In such examples where air may be injected into the pilot balloon 110 via a syringe, the syringe may first be drawn to fill the syringe with air, and while the syringe is still in the drawn position with air therein, the syringe may be inserted into the one-way valve 114 of the pilot balloon 110 to compress a spring of the one-way valve 114, causing the one-way valve 114 to open. Then the syringe may be compressed such that a plunger of the syringe pushes air out of the syringe, through the one-way valve 114 that is in the open position, into the pilot balloon 110, through the pilot line 112, and into the inflatable cuff 104.

The inclusion of a one-way valve 114 on the pilot balloon 110 may be beneficial for maintaining the inflatable cuff 104 in the inflated state. For example, once air has been introduced into the inflatable cuff 104 through the one-way valve 114 coupled to the pilot balloon 110, the one-way valve 114 may prevent air from flowing back out of the one-way valve 114 and into the atmosphere. Thus, the air may be held in the pilot balloon 110, the pilot line 112, and the inflatable cuff 104.

In particular, the pilot line 112 may be attached to the pilot balloon 110 at a first end of the pilot line 112, and the pilot line may be attached to the inflatable cuff 104 at a second end of the pilot line 112, where the first end of the pilot line 112 is opposite the second end of the pilot line 112.

Furthermore, as the pilot line 112 fluidly connects the pilot balloon 110 and the inflatable cuff 104, the pilot balloon 110 may expand when the inflatable cuff 104 is inflated. Thus, an inflation state of the pilot balloon 110 may be used to monitor an inflation state and/or inflation pressure of the inflatable cuff 104.

For example, if pilot balloon 110 is in an inflated state (i.e. the pilot balloon 110 is at least partially expanded due to air in the pilot balloon 110), this state of the pilot balloon 110 indicates that the inflatable cuff 104 that is fluidly connected to the pilot balloon 110 is also in the inflated state. Similarly, if the pilot balloon 110 is in a deflated state (i.e., the pilot balloon 110 is completely flat), then this deflated state of the pilot balloon 110 indicates that the inflatable cuff 104 that is fluidly connected to the pilot balloon 110 is also deflated.

Being able to monitor the inflation state of the inflation cuff 104 via the pilot balloon 110, where the pilot balloon 110 is outside the body of a patient when the ETT is positioned in the patient, may be particularly beneficial, as a view of the inflatable cuff 104 may be obscured when the ETT is positioned in a patient.

To transition the inflatable cuff 104 from the inflated state (as shown in FIG. 1B, for example) to the deflated state, a syringe in the compressed state may be inserted into the one-way valve 114 to compress a spring of the one-way valve 114 and open the one-way valve 114. Then, while the syringe is inserted in the one-way valve 114, the syringe may be drawn (retracted) to draw air from the inflatable cuff 104, the pilot line 112, and the pilot balloon 110 through the one-way valve 114 and into the syringe to deflate the inflatable cuff 104. Put another way, air may be evacuated out from the inflatable cuff 104, pilot line 112, and out of the pilot balloon 110, thus deflating the inflatable cuff 104.

It is noted that in at least one example, ETT system 100 and ETT system 102 may be the same ETT system. Thus, in at least one example, ETT system 100 is in the deflated state and ETT system 102 is the same ETT system as ETT system 100 but in the inflated state.

The ETT system 100 in the deflated state, in addition to being movable through the airway of the patient in order to intubate the patient, may also be removable from the airway of the patient to extubate the patient. In particular, as a diameter of the inflatable cuff 104 is smaller in the deflated state than when in the inflated state, the ETT system 100 in the deflated state may be removed from the airway of the patient. As such, the ETT system 100 in the deflated state may be removed from the airway of a patient or positioned in a desired location of the airway of the patient for subsequent inflation of the ETT system to anchor the ETT system in place and collect secretions.

In addition to the inflatable cuff 104 and the restrictor 106, other features that may be included in ETT system 100 may include an restrictor drainage assembly. Additionally or alternatively, a depression drainage assembly may be included above the inflatable cuff 104.

The restrictor drainage assembly may include a restrictor drainage bulb 124 and a restrictor drainage line 128. In at least one example, the restrictor drainage bulb 124 may include a collection reservoir 127 and an emptying cap 129. The restrictor drainage line 128 may couple the restrictor 106 to the restrictor drainage bulb 124 in at least one example. The drainage bulb cap 129 may be used to block and unblock an opening of the restrictor drainage bulb 124 for emptying the collection reservoir 127, in at least one example. Passive drainage occurs when the emptying cap 129 is open to air and fully expanded, and active drainage occurs when the air squeezed out of bulb and 129 is capped. In this situation, the negative pressure is created within the restrictor/drainage system with the help of inflated balloon. Additionally, the negative pressure created via the suctioning may help to enhance the seal between the inflatable cuff and the trachea wall 122.

The depression drainage assembly may or may not include a depression drainage bulb 115 and a depression drainage line 117. It is noted that depression drainage line 117, is only indicated schematically at FIGS. 1A and 1B to illustrate a general location of the depression drainage line 117, and details regarding the structure of depression drainage line 117 may be provided in relation to later figures. A first end of the depression drainage line 117 may be coupled to the depression drainage bulb 115, and a second end of the depression drainage line 117 that is opposite the first end of the depression drainage line 117 may be coupled to a collection region. Further, the depression drainage bulb 115 may include a collection reservoir 113 and an emptying cap 119. Alternatively, the decompression drainage line 117 has two ends, one end open to the lowest point above balloon 104, and the other end open to outside air with a removable cap. In some examples, the drainage line can also be used for suctioning drainage purposes, fluid irrigation, or medication delivery purposes.

Other features that may be included in the ETT system 100 may include a connector 130 and a Murphy eye 121, for example. The connector 130 may be included at an end of the ETT system 100 that is opposite an end of the ETT system 100 having the inflatable cuff 104 positioned thereon. The connector 130 may be utilized to connect the ETT system 100 to a ventilation system, in at least one example.

Murphy eye 121 may be an opening formed through the wall of the ETT 108 of the ETT system 100, and the Murphy eye 121 may be beneficial to allow ventilation through the ETT, for example. The Murphey eye 121 may be formed at an end of the ETT that is opposite an end that may include a connector 130. Further, in at least one example, the end of the ETT that includes the Murphy eye 121 may be beveled in shape. Such a beveled shape may make it easier to guide the ETT past the vocal chords of the patient, for example.

FIG. 1B shows cross-sectional view of the first ETT system 102 in an inflated state and positioned in a patient according to at least one example of the present disclosure. As discussed above, in at least one example, ETT system 100 and ETT system 102 may be a same ETT system. Thus ETT system 102 shown in FIG. 1B may be ETT system 100 in the inflated state.

ETT system 102 includes an inflatable cuff 104 and a restrictor 106 that is positioned on an exterior surface of the inflatable cuff 104. The restrictor 106 may be a 360° band that forms a ring which surrounds the exterior surface of the inflatable cuff 104, for example. However, in other examples the restrictor 106 may be a clamp, for example.

Regarding the inflatable cuff 104, in at least one example, the inflatable cuff 104 may be formed out of polyurethane. As discussed above, the inflatable cuff 104 at least partially surrounds a tube 108 of the ETT system 102, and the inflatable cuff 104 may be coupled to a pilot balloon 110 via pilot line 112. Further, at least a portion of the inflatable cuff 104 contacts the trachea wall and the sealing regions formed between the inflatable cuff 104 and the trachea wall 122 of the patient are formed completely around the trachea 123.

Specifically, the trachea 123 is tubular in shape, and the sealing regions formed by contact between the inflatable cuff 104 and the trachea wall 122 are in a 360° manner. Put another way, the inflatable cuff 104 extends outward 360° around the tube 108 of the ETT system 102 upon inflation. Thus, when the inflatable cuff 104 is positioned within the trachea 123, the trachea walls 122 encircle the inflatable cuff 104. As such, reference to protruding regions 118, 120 contacting the trachea wall 122 herein refer to the protruding regions 118, 120 extending outwards 360° and contacting the trachea wall 122 along all parts of the 360° outer surface of the protruding regions 118, 120.

Pilot balloon 110 may include a one-way valve 114 and may be used to adjust an amount of air in the inflatable cuff 104. For example, as discussed above, air may be introduced through the one-way valve 114 of the pilot balloon 110, through the pilot line 112, and into the inflatable cuff 104 in order to inflate the inflatable cuff 104. The one-way valve 114 may be a spring operated one-way valve 114, in at least one example. By introducing air into the inflatable cuff 104 through one-way valve 114, the air may be retained in the inflatable cuff 104 without escaping back through the pilot line 112 and the pilot balloon 110 into the atmosphere. As air is introduced into the inflatable cuff 104 the inflatable cuff 104 transitions to an inflated state, and a diameter of the inflatable cuff 104 may increase.

Once the diameter of the inflatable cuff 104 increases to be approximately the same diameter as an inner diameter of the restrictor 106, the restrictor 106 positioned on the exterior surface of the inflatable cuff 104 may restrict the inflatable cuff 104 from further expansion at the location where the restrictor 106 is positioned, and the inflatable cuff 104 may only continue to expand at regions upstream and downstream restrictor 106 as more air is introduced into the inflatable cuff 104. In some embodiments the restrictor 106 may at least partially stretch causing the restrictor 106 to increase in diameter due to the force of the inflatable cuff 104 on the restrictor 106 during inflation of the inflatable cuff 104. However, the restrictor 106 will still restrict the expansion of the inflatable cuff 104 at a location where the restrictor 106 and the inflatable cuff 104 are coupled, and the restrictor 106 will stretch less than the inflatable cuff 104 protruding regions upstream and downstream of the restrictor 106 expand. The restriction of the inflatable cuff 104 caused by the restrictor 106 may shape the inflatable cuff 104 to have a valley 116 that is positioned between protruding regions 118, 120 of the inflatable cuff 104.

When positioned in an airway of a patient, protruding region 118 of the inflatable cuff 104 may be an upstream protruding region of the inflatable cuff 104, while protruding region 120 may be a downstream protruding region of the inflatable 104, where upstream and downstream are defined based on a direction of air flow during inhalation.

In the inflated state and when positioned in an airway of the patient, the protruding regions 118, 120 of the inflatable cuff 104 contact a trachea wall 122 of the patient, while the valley 116 is recessed away from the trachea wall 122 so that the valley 116 is not contact with the trachea wall 122.

It is noted that the trachea 123 is tubular in shape and that when the protruding regions 118, 120 of the inflatable cuff 104 contact the trachea wall 122, the protruding regions 118, 120 have expanded outward 360° from a point where the inflatable cuff 104 is in contact with the tube 108 of the ETT system 102.

Thus, protruding region 118 expands upon inflation when the ETT system 102 is positioned in a patient to contact trachea wall 122 and form a first sealing region. Similarly, protruding region 120 expands upon inflation when the ETT system 102 is positioned in the patient to contact trachea wall 122 and form a second sealing region. The valley 116 of the inflatable cuff 104 that is formed directly between the first protruding region 118 and the second protruding region due to the restriction of the inflatable cuff 104 forms an unsealed region between the first sealing region and the second sealing region.

The unsealed region formed due to the valley 116 of the inflatable cuff 104 forms a collection region 126 that collects secretions that may leak past the first sealing region formed by the contact between the first protruding region 118 and the trachea wall 122.

Additionally, in at least one example, a depression may be formed on a top surface of the inflatable cuff 104 to form another collection region, which will be discussed in more detail below.

The particular shaping of the inflatable cuff 104 to include protruding regions 118, 120 of the inflatable cuff that contact the trachea wall 122 and to include a valley 116 positioned between the protruding regions 118, 120 of the inflatable cuff 104 being recessed away from the trachea wall 122 (i.e., not contacting the trachea wall 122), the inflatable cuff 104 may advantageously provide multiple sealing regions. In particular, the upstream protruding region 118 may contact a trachea wall 122 to form a first sealing region, and the downstream protruding region 120 of the inflatable cuff 104 may contact the trachea wall 122 to form a second sealing region.

Thus, via the shaping of the inflatable cuff 104, if secretions leak past the first sealing region, the second sealing region positioned downstream of the first sealing region may prevent these secretions from leaking further downstream in the airway of the patient.

Collection region 126 formed between valley 116 of the inflatable cuff 104 and the trachea wall 122 serves to retain secretions that may leak downstream of the first sealing region and prevent these secretions from leaking downstream past the second sealing region. Specifically, the collection region 126 may be surrounded by the restrictor 106 that forms valley 116, the trachea wall 122, the first protruding region 118, and the second protruding region 120 to prevent secretions that leak downstream past the first protruding region 118 from leaking downstream past the second protruding region 120 and into the bronchi 125a, 125b of the patient.

Thus, due to the shaping of the inflatable cuff 104 achieved by the restrictor 106, secretions may be prevented from being aspirated and undesirable biofilms may be prevented from forming. Additionally, in embodiments where the restrictor 106 is coupled to the inflatable cuff 104 to achieve this shaping, the above discussed advantages may be achieved in a simple manner using only a single inflatable cuff and a restrictor positioned on an outside of the inflatable cuff.

Furthermore, in at least one example, the secretions that may be collected in the collection region 126 formed between valley 116 of the inflatable cuff 104 and the trachea wall 122 may be removed via a restrictor drainage bulb 124. For example, restrictor drainage bulb 124 may be coupled with restrictor 106 (e.g., a band) via an restrictor drainage line 128. In particular, a first end of the restrictor drainage line 128 may be attached to the restrictor drainage bulb 124 and a second end of the restrictor drainage line may be attached to the restrictor 106. In at least one example, the restrictor drainage line 128 may be attached to a tail of the restrictor 106.

In order to drain (i.e., remove) secretions collected in the valley 116 of the inflatable cuff 104, the restrictor drainage bulb 124 may be used to apply a negative pressure to the collection region 126 formed between the valley 116 and the trachea wall 122. For example, in at least one embodiment, applying negative pressure to the collection region 126 via the restrictor drainage bulb 124 may include detaching the restrictor drainage bulb 124 from the restrictor drainage line 128, compressing the restrictor drainage bulb 124 (e.g., compressing the collection reservoir 127) while the restrictor drainage bulb 124 is detached from the restrictor drainage line 128, and then attaching the compressed restrictor drainage bulb 124 to the restrictor drainage line 128.

The compressed restrictor drainage bulb 124 that is attached to the restrictor drainage line 128 may then decompress, causing a negative pressure to be applied to the collection region 126. Application of negative pressure to the collection region 126 via restrictor drainage bulb 124 may cause secretions collected in the collection region 126 to be suctioned into the collection reservoir 127 of the restrictor drainage bulb 124.

For example, in embodiments that include a restrictor drainage bulb 124 that is attached to the restrictor 106, the restrictor 106 may include one or more cavities. Thus, when a negative pressure is applied to the collection region 126 via the restrictor drainage bulb 124, the negative pressure may cause secretions collected at collection region 126 to be suctioned through the one or more cavities of the restrictor 106, through the restrictor drainage line 128, and into the collection reservoir 127 of the restrictor drainage bulb 124. The restrictor drainage bulb 124 may then be detached from the restrictor drainage line 128, and secretions that may have been collected in the collection reservoir 127 may be emptied through emptying cap 129.

Applying negative pressure via the restrictor drainage bulb 124 to this collection region 126 that is substantially sealed in the airway may result in the restrictor drainage bulb 124 carrying out a longer continuous suctioning process for a single compression of the restrictor drainage bulb 124 compared to other approaches which may have suctioned secretions from an area of the airway that is not substantially sealed.

This prolonged and continuous suctioning process for a single compression of the restrictor drainage bulb 124 may be beneficial, as an amount of staff time required to provide continuous suctioning for removal of secretions may be reduced. Furthermore, this prolonged and continuous suctioning process for a single compression of the restrictor drainage bulb 124 may be achieved in a simple manner without having to rely on a device that is separate from the ETT system.

In addition to collection region 126, another collection region may be formed by a shaping of a top surface of the inflatable cuff 104. For example, the inflatable cuff may be anchored to an exterior of the wall of tube 108, and upon inflation of the inflatable cuff 104, the anchoring of the inflatable cuff 104 to the exterior of the wall of tube 108 may cause a depression to be formed in a top surface of the inflatable cuff 104. This depression may collect secretions, and these secretions collected in the depression may be removed via a depression drainage assembly. For example, the depression drainage assembly may include a depression drainage line 117. A first end of the depression drainage line 117 may connect to a depression drainage bulb 115, and a second end of the depression drainage line 117 may open into a depression formed into a top surface of the inflatable cuff 104. The depression drainage bulb 115 may include a collection reservoir 113 and cap 119. In at least one example, the cap 119 may be a screw-on cap. When needed cap 119 may be opened to and one or more of suction and irrigation may be performed in a sterile fashion. More details regarding the collection region formed by the depression are discussed below.

Further, though ETT systems 100 and 102 are shown with a single restrictor positioned over an outer surface of a single inflatable cuff, it is noted that multiple restrictors may be positioned over the single inflatable cuff. In examples where multiple restrictors may be positioned over the single inflatable cuff, multiple valleys, and thus multiple collection and drainage point may be formed.

For example, in embodiments where multiple restrictors may be positioned over a same inflatable cuff, when the inflatable cuff is in an inflated state, the inflatable cuff may include a plurality of valleys, with each valley positioned directly between protruding regions. For example, a first valley may be positioned directly between a first protruding region and a second protruding region of an inflatable cuff, and a second valley may be positioned directly between the second protruding region and a third protruding region of the same inflatable cuff. Each of the valleys may form an unsealed region in the airway of the patient positioned directly between two protruding regions. Thus, in such examples where there may be multiple restrictors positioned on a single inflatable cuff, when the ETT system is positioned in an airway of a patient and the single inflatable cuff is in an inflated state, each of the plurality of valleys may form a separate collection region. In particular, each of valleys may form a collection region between the trachea wall 122 of the patient and the valleys.

Further, each of these collection region formed by the valleys may include at least one drainage point to drain secretions collected at the collection region. For example, any one or combination of the drainage mechanisms described above may be implemented to form the at least one drainage point at each collection region, such as a drainage bulb suctioning or syringe suctioning.

Furthermore, in at least one example, an ETT system may include a plurality of inflatable cuffs. In such examples where the ETT system may include a plurality of inflatable cuffs, each separate inflatable cuff may be connected to its own inflation assembly, as described above. Additionally, at least one of the plurality of inflatable cuffs may include a restrictor positioned on an outer surface of the inflatable cuff, the restrictor surrounding the inflatable cuff and restricting expansion of the inflatable cuff to shape the inflatable cuff such that the inflatable cuff includes a valley.

Turning now to FIG. 1C, FIG. 1C shows an exploded cross-sectional view of region A 101 of the first example ETT system. As shown in the exploded cross-sectional view of region A 101, trachea wall 122 comprises trachea cartilage 142 and annular ligaments 140. The trachea cartilage 142 is denoted by dotted shading, while the annular ligaments 140 are unshaded.

The trachea wall comprising a combination of trachea cartilage 142 and the annular ligaments 140 creates problems in regards to sealing the airway of the patient. In particular, the trachea cartilage is hard compared to the annular ligaments 140, and as the trachea wall comprises both hard regions and soft tissue regions, it may be difficult to form a perfect seal between the trachea wall and an inflatable cuff of an ETT system, as deformation of the annular ligaments 140 may be greater than a deformation of the trachea cartilage 142 for a same amount of force.

However, by including an inflatable cuff 104 that has a restrictor 106 restricting a region of the inflatable cuff 104 from expanding, such that the inflatable cuff 104 is shaped to include a valley 116 formed between two protruding regions of the inflatable cuff 104, better sealing of the airway may be achieved to prevent secretions from being aspirated, where aspiration may occur if secretions leak downstream both the first sealing region 144 and the second sealing region 146. Further it is noted that in examples where the ETT system comprises a tail 176, tail 176 may be in contact with the trachea wall 122 directly between the first protruding region 118 of the inflatable cuff 104 for a portion of a first sealing region 144. For example, the first protruding region 118 of the inflatable cuff 104 may contact the wall of the trachea 122 to form a seal between the inflatable cuff 104 and the trachea 122, and the first protruding region 118 may contact the tail 176, the tail 176 positioned between the trachea wall 122 and the first protruding region 118. It is noted that upstream and downstream are defined based on a direction of airflow during inhalation. For example, as upstream and downstream are defined based on the direction of airflow during inhalation, the first sealing region 144 is upstream the second sealing region 146. For reference, a general direction of airflow at a trachea of a patient during inhalation 105 is shown for reference.

Due to the shaping of the inflatable cuff 104 caused by the restrictor 106, a first sealing region 144 may be formed between the first protruding region 118 of the inflatable cuff 104 and the trachea wall 122, and a second sealing region 146 may be formed between the second protruding region 120 of the inflatable cuff 104 and the trachea wall 122. In particular, the first sealing region 144 and the second sealing region may be formed where the first protruding region 118 and the second protruding region 120 contact the trachea wall. In examples where a tail 176 is included, a portion of the first sealing region 144 may further comprise a region where tail 176 is positioned between the inflatable cuff 104 and the trachea wall 122, the inflatable cuff 104 further contacting the trachea wall 122 on either side of the tail 176 to form a sealing region to prevent secretions from leaking downstream of the first sealing region 144.

However, even if an imperfect seal (i.e., a seal where there is not complete contact between the inflatable cuff and the trachea wall) is formed at the first sealing region 144 allowing secretions to leak downstream past the first sealing region 144, such secretions may be prevented from being aspirated due to the second sealing region 146. In particular, the second sealing region 144 may act as a second line of defense to prevent aspiration, as secretions that leak past the first sealing region 144 may be trapped upstream of the second sealing region 146 in unsealed region 158.

These secretions that leak past the first sealing region 144 and are prevented from traveling downstream of the second sealing region 146 may be trapped between the restrictor 106, the trachea wall 122, and the surfaces of the protruding regions 118, 120 that are immediately adjacent upstream and downstream of the restrictor 106.

Put another way, secretions that leak downstream the first sealing region 144 may be trapped upstream of the second sealing region 146 at collection region 126. In particular, at unsealed region 158, a bottom surface 154 of the first protruding region 118, a top surface 156 of the second protruding region 120, trachea wall 122, and the restrictor 106 may surround collection region 126. Thus, secretions that may leak past the first sealing region 144 formed between the first protruding region 118 of the inflatable cuff 104 and the trachea wall 122 may collect on a top surface 156 of the second protruding region 120 and be retained by the top surface 156 of the second protruding region 120, the restrictor 106, and the trachea wall 122.

As such, in at least one example, though the first sealing region 144 may not be a complete seal, due to the second sealing region 146, the inflatable cuff 104 may form an overall substantially hermetic seal. Further, in at least one example, the combination of the first sealing region 144 and the second sealing region 146 with the unsealed region 158 therebetween may form a hermetic seal in the trachea 123.

After trapping the secretions at collection region 126, the secretions may be drained from collection region 126. For example, in at least one embodiment secretions trapped at collection region 126 may be suctioned through one or more cavities 138 formed into restrictor 106 into an interior space 152 of the restrictor 106, through restrictor drainage line 128, and into collection reservoir 127 of restrictor drainage bulb 124. In at least one example, the secretions may be suctioned from collection region 126 by applying negative pressure via restrictor drainage bulb 124, as discussed above.

Further, the configuration of the one or more cavities 138 of the restrictor 106 may be varied. For example, in some embodiments there may only be a single cavity 138 formed into the restrictor 106. However, in other embodiments there may be multiple cavities 138 formed into the restrictor 106. One or more of an arrangement of the cavities 138 and a shaping of cavities 138 may be varied as well.

The secretions that are drained into collection reservoir 127 may then be emptied from the restrictor drainage bulb 124 by opening an emptying cap 129 and emptying the drained secretions out of the collection reservoir 127. The sample can be used for further analysis or culture for bacteria. In at least one example, the restrictor drainage bulb 124 may be removable from the restrictor drainage line 128 to facilitate such emptying of the collection reservoir 127. Thus, in such examples where the restrictor drainage bulb 124 may be removable from the restrictor drainage line 128, emptying the restrictor drainage bulb 124 may first include decoupling the restrictor drainage bulb 124 from the restrictor drainage line 128, opening emptying cap 129, and emptying the collection reservoir 127 through the opened emptying cap. Following emptying out the restrictor drainage bulb 124, the restrictor drainage bulb 124 may then be recoupled to the restrictor drainage line 128 and the emptying cap 129 may be closed.

Regarding FIG. 1D, FIG. 1D shows an exploded view of region B 103 of the first example ETT system. Similar to region A 101, region B 103 also includes the first sealing region 144 and the second sealing region 146, where the first sealing region 144 is upstream of the second sealing region 146 based on the direction of airflow during inhalation. The trachea wall 122 is more curved in shaped at region B 103 than in region A 101, and the inflatable cuff 104 conforms to the curvature of the trachea wall 122.

Turning now to FIG. 2, FIG. 2 shows a schematic view of secretion flow through an ETT system 200 positioned in a patient and that is in an inflated state according to at least one embodiment of the disclosure. In particular, FIG. 2 is a cross-sectional view of ETT system 200 that is positioned in a patient and in an inflated state, where axis 150 is a midline of the elongated tube of the ETT system 200. Specifically, inflatable cuff 104 of ETT system 200 is positioned in a trachea 123 of the patient. ETT 108 of the ETT system 200 may comprise an interior space 210 that defines an airflow through ETT 108. Interior space 210 may allow air to pass through the ETT 108 from upstream of the inflatable cuff 104 to downstream of the inflatable cuff 104, even when the inflatable cuff 104 is in an inflated state.

Secretions 174 that are trapped at collection region 126 during a draining event are flowed towards the restrictor 106, as generally indicated by flow directional arrows 212. For example, during a draining event, negative pressure may be applied to collection region 126 to suction secretions out of the collection region 126. Negative pressure may be applied to collection region 126 via a restrictor drainage assembly, such as the restrictor drainage assembly described in relation to FIG. 1A, for example.

Upon applying a negative pressure to collection region 126, secretions 174 collected at collection region 126 may be suctioned through one or more cavities 138 of and interior space 152 of restrictor 106, through a restrictor drainage line, and into a restrictor drainage bulb (restrictor drainage line and restrictor drainage bulb are not shown in FIG. 2), thus causing secretions 174 collected at collection region 126 to flow in a general direction of flow directional arrows 212.

Further, in addition to collection region 126, in at least one embodiment, a top center portion of inflatable cuff 104 may be anchored to tube 108 via at least one anchoring point such that a depression 202 forms upon inflation of the inflatable cuff 104, where inflation of the inflatable cuff 104 includes introducing air into the lumen 206 of inflatable cuff 104, where lumen 206 is surrounded by walls 208 of inflatable cuff 104.

Put another way, in at least one example, inflatable cuff 104 includes at least one anchoring point to attach the inflatable cuff 104 to tube 108, and as the inflatable cuff 104 is inflated causing the inflatable cuff 104 to expand in size, the anchoring point connecting the inflatable cuff 104 to the tube 108 may prevent expansion in a center top portion of the inflatable cuff 104. Thus, depression 202 may be formed in the top surface of the inflatable cuff 104. Depression 202 may be concave relative to the top surface of the inflatable cuff 104. This concave shaping of depression 202 relative to the top surface of the inflatable cuff 104 may serve as collection region of the inflatable cuff 104. In particular, the shaping of depression 202 to be concave relative to the top surface of inflatable cuff 104 may cause secretions 174 to collect in the depression 202 due to the force of gravity 168.

Secretions 174 collected in depression 202 may be drained via an external device in at least one example. For example, secretions 174 collected in depression 202 may be suctioned via a syringe or other external suctioning device. In at least one example, secretions 174 collected in depression 202 may be suctioned through depression drainage line 117 and into a collection reservoir 113 of the depression drainage bulb 115.

Thus, the depression 202 may form a first collection region and collection region 126 formed between valley 116 and trachea wall 122 may be a second collection region. Further, each of the first collection region and the second collection region may have a drainage point provided therein.

Furthermore, in at least one example, multiple drainage points may be included to drain a single collection region. For example, a plurality of restrictor drainage bulbs may each be connected to restrictor 106 via respective restrictor drainage lines to all drain collection region 126. The use of multiple drainage points to drain a single collection region may be beneficial to more quickly drain the collection region.

By including a plurality of collection regions that collect secretions 174, where each of the collection regions includes at least one drainage point, aspiration may be more effectively prevented.

Alternatively, in some examples the ETT system 200 may only include a single collection region 126, and at least one drainage point connected to the collection region 126.

Turning now to FIG. 3A, FIG. 3A shows a side view of a second example ETT system 300 in an inflated state according to at least one embodiment of the present disclosure. ETT system 300 includes a restrictor drainage bulb 124 connected to restrictor drainage line 128 at a first end of restrictor drainage line 128. A second end 306 of restrictor drainage line 128 that is opposite the first end of the restrictor drainage line 128 may be connected to restrictor 106, where restrictor 106 includes one or cavities formed therethrough.

In some examples, the restrictor drainage line 128 may be formed into a wall of tube 108 of the ETT system 300. In such examples where the restrictor drainage line 128 may be formed into a wall of tube 108 of the ETT system 300, the first end of the restrictor drainage line 128 may connect to restrictor drainage bulb 124, the second end of the restrictor drainage line 128 may connect to the restrictor 106, and at least a portion of the restrictor drainage line 128 between the first end and the second end of the restrictor drainage line 128 may be integrated into the tube 108 wall.

At least a portion of the restrictor drainage line 128 may be integrated into the wall of the tube 108 of ETT system 300. For example, an restrictor drainage line opening may be formed into the wall of the tube 108 of ETT system 300 to receive at least a portion of the restrictor drainage line 128. Therefore, in such examples, at least a portion of the restrictor drainage line 128 may be surrounded by the wall of tube 108.

For example, in embodiments where an restrictor drainage line opening may be formed into the wall of tube 108 to receive restrictor drainage line 128, a first lateral restrictor drainage line port may be formed into the tube 108 that opens through an outer surface of the tube 108 to enable the restrictor drainage line 128 to enter the wall of tube 108, where the first lateral restrictor drainage line port does not open into an interior space 210 (shown in FIG. 2) of tube 108, and where the first lateral restrictor drainage line port may be near an end of the tube 108 that is external to a body of a patient when the ETT system 300 is positioned in an airway of the patient. It is noted that the interior space 210 of tube 108 may be an opening of tube 108 that is encircled by walls of tube 108. In examples such as the above, the first lateral restrictor drainage line port may receive the restrictor drainage line 128.

The first lateral restrictor drainage line port, which is surrounded by the wall of tube 108, may connect with a first end of a longitudinal restrictor drainage line port formed inside the tube 108 in a continuous manner, where the longitudinal restrictor drainage line port is also surrounded by the wall of tube 108. Put another way, the first lateral restrictor drainage line port formed into the wall of tube 108 may open into the longitudinal restrictor drainage line port, where the longitudinal restrictor drainage line port is also formed into the wall of tube 108. For example, the longitudinal restrictor drainage line port may be surrounded by the wall of tube 108 and may run along a substantial length of tube 108.

A second end of the longitudinal restrictor drainage line port that is opposite the first end of the longitudinal restrictor drainage line port may connect with a second lateral restrictor drainage line port in a continuous manner, where the second lateral restrictor drainage line port opens through an outer surface of the tube 108 without opening into an interior space 210 (shown in FIG. 2, for example) of the tube 108, and where the second lateral restrictor drainage line port is surrounded by the wall of the tube 108. As such, the first lateral restrictor drainage line port and the second lateral restrictor drainage line port may be connected by the longitudinal restrictor drainage line port. The second lateral restrictor drainage line port may be near an end of ETT system 300 that includes inflatable cuff 104.

Thus, the restrictor drainage line 128 may be received in the openings formed in the wall of the tube 108 and at least a portion of the restrictor drainage line 128 may be surrounded by the wall of the tube 108. Specifically, at least a portion of restrictor drainage line 128 may be received in the first lateral restrictor drainage line port, the longitudinal restrictor drainage line port, and the second lateral restrictor drainage line port, where all of the ports are openings are formed into the wall of tube 108. Such integration of at least a portion of the restrictor drainage line 128 into the wall of the tube 108, may be advantageous to help to keep the ETT system 300 compact.

Alternatively, in another embodiment the restrictor drainage line 128 may be formed as a single unitary piece with the tube 108 of the ETT system 300. For example, a first segment of restrictor drainage line 128 may be connected to the first lateral restrictor drainage line port, and another segment of restrictor drainage line 128 may be connected to the second lateral restrictor drainage line port, where the longitudinal restrictor drainage line port connects the first lateral restrictor drainage line opening and the second lateral restrictor drainage line opening, as opposed to the restrictor drainage line 128 being received by the restrictor drainage line ports.

Alternatively, in at least one example the restrictor drainage line 128 may not be integrated into the wall of the tube 108 at all, and the restrictor drainage line 128 may instead be entirely positioned outside of the ETT system 300. For example, the first end of the restrictor drainage line 128 may be attached to the restrictor drainage bulb 124 and the second end of the restrictor drainage line 128 may be attached to the restrictor 106, where the restrictor drainage line 128 is positioned outside the tube 108 of the ETT system 300 and outside the inflatable cuff 104. Such embodiments may be beneficial for simplifying a process for manufacturing the ETT system 300, for example.

In at least one embodiment, the wall of tube 108 may include one or more openings formed therein in addition to or alternatively to restrictor drainage line openings for the restrictor drainage bulb 124 assembly. For example, in addition to one or more ports being formed into the wall of tube 108 for an restrictor drainage assembly, ports may be formed into the wall of tube 108 as a part of one or more of the depression drainage assembly and the inflation assembly. For example, ports formed into the wall of tube 108 may receive at least a portion of depression drainage line 117. Additionally or alternatively, ports formed into the wall of tube 108 may receive at least portion of the pilot line 112.

In embodiments where there may be multiple restrictor drainage lines, depression drainage lines, or pilot lines of an ETT system, ports may be formed into the wall of the tube 108 for each of these restrictor drainage lines, depression drainage lines, and pilot lines of the ETT system. Alternatively, only some of restrictor drainage lines, depression drainage lines, and pilot lines of an ETT system may be integrated into the wall of the tube.

For example, ports for receiving each of the multiple restrictor drainage lines, depression drainage lines, and pilot lines of an ETT system may be formed into the wall of tube 108. Alternatively, rather than receiving the restrictor drainage lines, depression drainage lines, and pilot lines in ports formed into the wall of tube 108, at least one of the restrictor drainage lines, depression drainage lines, and pilot lines may not be received by the ports but rather connected to the ports. Put another way, instead of the wall of tube 108 including ports for receiving the one or more of the restrictor drainage lines, depression drainage lines, and pilot lines, the ports formed into the wall of tube 108 replace a portion of the restrictor drainage lines, depression drainage lines, and pilot lines.

Furthermore, although FIG. 3A shows inflatable cuff 104 as substantially symmetrical, in at least one embodiment the inflatable cuff 104 may be asymmetrical. For example, the inflatable cuff 104 may be shaped asymmetrically to more closely mimic a shape of a trachea. Additionally, inflatable cuff 104 may be deformed to a shape of a trachea of a patient upon positioning and inflation of the inflatable cuff in the patient. Thus, though inflatable cuff 104 may be symmetrical when not positioned in a patient, the inflatable cuff 104 may be deformed from being symmetrical in shape to being asymmetrical in shape if inflated when positioned in a patient.

Regarding FIG. 3B, FIG. 3B shows a view of the third example ETT system 302 in a deflated state. In at least one embodiment, ETT system 302 in the deflated state may be a same ETT system as ETT system 300, where the inflatable cuff 104 is in the deflated state, as opposed to the inflated state.

Turning now to FIG. 3C, FIG. 3C shows a first cross-sectional view 304 taken along axis 308 of the third example ETT system (axis 308 is shown in FIG. 3A). As shown in cross-sectional view 304, the wall of tube 108 includes multiple ETT ports formed therein. For example, the wall of tube 108 includes a pilot line port 312, a depression drainage line port 314, and an restrictor drainage line port 316, and each of these ports may be positioned approximately 120° apart. However, in other embodiments, a spacing of the ports may be more or less than approximately 120° apart to accommodate particular configurations of the depression drainage line, restrictor drainage line, and pilot line of the ETT. Further, in some embodiments there may be more or less than three ports. It is noted that although the wall of the ETT 108 is shown comprising ports that may house or that may form at least part of the drainage lines/inflation lines of the ETT system, in at least one example one or more of the drainage lines/inflation lines of the ETT system may be attached to the ETT inside an interior space that defines an airflow through the ETT, such as interior space 210, for example. Additionally or alternatively, one or more of the drainage lines/inflation lines of the ETT system may be attached to an exterior surface of the tube 108. In at least one embodiment, the ETT 108 may not comprise any ports, and the wall of the ETT 108 may instead be solid. Thus, all of the drainage lines and inflation lines may be coupled to either an exterior surface of the ETT 108 or to an interior surface of the ETT 108. Such examples may simplify manufacturing of the ETT 108.

As discussed above, the ports formed into the wall of tube 108 may receive any one of pilot lines, depression drainage lines, and restrictor drainage lines of an ETT. For example, the pilot line port 312 may receive a pilot line, such as pilot line 112. Similarly, the depression drainage line port 314 may receive a depression drainage line, such as depression drainage line 117, and the restrictor drainage line port 316 may receive an restrictor drainage line, such as restrictor drainage line 128.

In embodiments where there may be more than three total of pilot lines, depression drainage lines, and restrictor drainage lines, there may be more than three ports formed into the wall of tube 108. As such, in at least one example, the number of ports included in the wall of tube 108 may correspond to a total number of pilot lines, depression drainage lines, and restrictor drainage lines of an ETT, where each pilot line, depression drainage line, and restrictor drainage line includes a corresponding port formed into the wall of tube 108. Examples where all of the pilot lines, the depression drainage lines, and the restrictor drainage lines of an ETT include a corresponding port formed into a wall of the tube 108 of the ETT may advantageously result in an overall compact ETT.

Alternatively, in other embodiments, only some of the total number of pilot lines, depression drainage lines, and restrictor drainage lines of an ETT may have a corresponding port formed into the wall of tube 108. Thus, a total number of ports formed into the wall of the tube 108 may be less than the total number of pilot lines, restrictor drainage lines, and depression drainage lines. For example, fewer than three ports may be included in the wall of tube 108, even though there may be three or more pilot lines, restrictor drainage lines, and depression drainage lines total. Such examples where only some of the total number of pilot lines, depression drainage lines, and restrictor drainage lines of an ETT have a corresponding port formed into the wall of tube 108 may be beneficial for simplifying construction of the ETT while still ensuring that the ETT is more compact than examples where there may be no ports formed into the wall of the tube 108.

In still another embodiment of the present disclosure, no ports may be formed into the wall of tube 108 of the ETT system, and all of the pilot lines, depression drainage lines, and restrictor drainage lines of the ETT system may be external to the wall of tube 108. Such examples where wall of tube 108 may not include any ports may result in an overall more simple construction for manufacturing the ETT system compared to examples where one or more ports may be formed into the wall of the tube 108 of the ETT system.

Further, it is noted that although the cross-sectional view 304 taken at axis 308 shows three ports (312, 314, 316), the number of ports formed into the wall of the tube 108 may vary depending upon a location along a length of the tube 108. In at least one example, the variance in the number of ports formed into the wall of tube 108 along the length of the tube 108 may be due to the ports opening through an exterior of the tube 108.

For example, a first end of a pilot line port 312 may open through an exterior of the tube 108 near an end of the ETT that is exterior to a body of a patient when the ETT is positioned in the patient, and a second end of the pilot line port 312 may open into the lumen of the inflatable cuff, such as inflatable cuff 104. Thus, the wall of the tube 108 may only include the pilot line port 312 formed therein between the first end and the second end of the pilot line port 312, and a remainder of the wall of the tube 108 may not include the pilot line port 312 formed therein.

Additionally or alternatively, in some examples a first end of a depression drainage line port 314 may open through an exterior of the tube 108 near an end of the ETT that is exterior to a body of a patient when the ETT is positioned in the patient, and a second end of the depression drainage line port 314 may open into a depression formed into a top of the inflatable cuff, such as depression 202. Thus, the wall of the ETT tube 108 may only include the depression drainage line port 314 formed therein between the first end and the second end of the depression drainage line port 314, and a remainder of the wall of the tube 108 may not include the depression drainage line port 314 formed therein.

Similar to the pilot line port 312 and the depression drainage line port 314, in at least one example a first end of an restrictor drainage line port 316 may open to an exterior of the tube 108 near an end of the ETT that is exterior to a body of a patient when the ETT is positioned in the patient, and a second end of the restrictor drainage line port 316 may open into a restrictor of the ETT, such as restrictor 106. As such, the wall of the tube 108 may only include the restrictor drainage line port 316 between the first end and the second end of the restrictor drainage line port 316, and a remainder of the wall of the tube 108 may not include the restrictor drainage line port 316 formed therein.

Turning now to FIG. 3D, FIG. 3D shows a second cross-sectional view 306 of the third example ETT system according to at least one embodiment of the present disclosure taken along axis 310 of FIG. 3A, where axis 310 passes through a restrictor, such as restrictor 106.

As shown in cross-sectional view 306, a restrictor 106 may at least partially surround inflatable cuff 104. For example, restrictor 106 may completely surround inflatable cuff 104. Examples where a restrictor completely surrounds the inflatable cuff 104 may be beneficial to ensure that the entire trachea is sealed off with multiple sealing regions.

Restrictor 106 may be tubular in shape in at least one example, and restrictor 106 may have an interior space 152. Put another way, the restrictor 106 may have a hollow interior.

Interior space 152 of restrictor 106 is encircled by an interior surface of the restrictor 106, where the interior surface of the restrictor 106 is a surface of the restrictor that is opposite an external surface of the restrictor 106. The interior space 152 of restrictor 106 may be continuous through the entire restrictor 106 in some examples. For example, interior space 152 of restrictor 106 may run through an entire interior of restrictor 106 such that the entire restrictor 106 is hollow. Such examples where the interior space 152 of restrictor 106 is continuous through the entire restrictor 106 may be beneficial for increasing flow through the restrictor 106 for drainage events. However, in other examples, only a portion of the restrictor 106 may be hollow and have an interior space 152. Examples where only a portion of the restrictor may have an interior space 152 may be beneficial for increasing a strength of the restrictor 106, as the restrictor wall may be thickened at some regions of the restrictor, for example.

Thus, the restrictor 106 may be a band or other restrictor that at least partially surrounds inflatable cuff 104, and the restrictor 106 itself may be at least partially hollow. Further, in some examples restrictor 106 may completely surround inflatable cuff 104, and the restrictor may form a complete loop, where the restrictor 106 itself may be tubular in shape.

Additionally, restrictor 106 may comprise one or more cavities 138 that open through a wall of the restrictor 106 and into the interior space 152 formed into restrictor 106. In some examples, the one or more cavities 138 that open through the wall of the restrictor 106 may open through a portion of the wall of the restrictor 106 that is coupled to the inflatable cuff 104 and through a portion of the wall of the restrictor 106 that is not coupled to the inflatable cuff 104. However, in at least one embodiment, the one or more cavities 138 formed through the wall of the restrictor 106 may be configured such that the portion of the wall of the restrictor 106 that is coupled to the inflatable cuff 104 does not comprise cavities 138 therein, and such that only the portion of the wall of the restrictor 106 that is not coupled to the inflatable cuff 104 may include one or more cavities 138 therein. As shown in FIG. 3D, the one or more cavities 138 may be spaced symmetrically at regular intervals around the restrictor 106. However, in at least one example the one or more cavities 138 may be asymmetrically spaced around the restrictor 106 at irregular intervals. Further details regarding example configurations for the one or more cavities 138 are described in more detail at FIGS. 6-7.

As discussed above, restrictor 106 is coupled to an exterior surface of inflatable cuff 104 and restricts inflatable cuff 104 from expanding at a point where the restrictor 106 is coupled to the inflatable cuff 104. Thus, as restrictor 106 prevents expansion at a point where the restrictor 106 is coupled to the inflatable cuff, the restrictor 106 outer diameter 318a, 318b may be an outermost diameter at axis 310 (axis 310 is shown in FIG. 3A).

In addition to restrictor outer diameter 318a, 318b, restrictor 106 may further include an inner diameter 320a, 320b. The restrictor inner diameter 320a, 320b may define an outer diameter of inflatable cuff 104, in at least one example. For example, restrictor inner diameter 320a, 320b may define the outer diameter of inflatable cuff 104, as restrictor 106 may at least partially surround and be coupled to inflatable cuff 104 to restrict expansion of inflatable cuff 104 at a location where inflatable cuff 104 is coupled to the restrictor. Thus, 320*a*, 320*b* may also be an outer diameter of inflatable cuff 104.

Furthermore, inflatable cuff inner diameter 322*a*, 322*b* may be approximately a same diameter as tube 108 outer diameter, and tube inner diameter 324*a*, 324*b* may be a diameter of an interior space 210 of tube 108, where the interior space 210 defines an airflow path through an ETT.

Turning now to FIG. 4A, FIG. 4A shows a view of a fourth example ETT system 400 including a plurality of inflatable cuffs. ETT system 400 is very similar to the previously described example ETT systems with the exception that ETT system 400 comprises a plurality of inflatable cuffs 104*a*, 104*b*, where inflatable cuff 104*a* is a separate inflatable cuff from inflatable cuff 104*b*. Furthermore, each of inflatable cuffs 104*a*, 104*b* is coupled to a separate inflation assembly. For example, pilot line 112*a* couples inflatable cuff 104*a* to pilot balloon 110*a*, where pilot balloon 110*a* includes a one-way valve 114*a*. Similarly, pilot line 112*b* couples inflatable cuff 104*b* to pilot balloon 110*b*, where pilot balloon 110*b* includes a one-way valve 114*b*. Though example ETT system 400 is shown with two separate inflatable cuffs, it is appreciated that more separate inflatable cuffs may be included.

Restrictor 106 is positioned directly between inflatable cuff 104*a* and inflatable cuff 104*b*. Further, rather than restrictor at least partially surrounding inflatable cuff 104*a* or inflatable cuff 104*b*, the restrictor 106 may instead be coupled to tube 108. For example, restrictor 106 may be coupled to tube 108 without anything positioned between restrictor 106 and tube 108 with the exception of adhesive, in some examples. It is noted that any one or combination of the above approaches for coupling a restrictor to an inflatable cuff may also be applied for coupling the restrictor 106 to tube 108. Thus, ETT system 400 may have a shaping to collect secretions upstream of the bronchi of a patient via the separate inflatable cuffs 104*a*, 104*b* as well as a simple and robust draining system via restrictor 106.

In at least one example, in addition to the restrictor 106 being coupled to the tube 108 between the separate inflatable cuffs 104*a*, 104*b*, one or both of the separate inflatable cuffs 104*a*, 104*b* may also have one or more restrictors coupled thereto.

Turning to FIG. 4B, FIG. 4B shows a cross-sectional view 404 of the fourth example ETT system taken along axis 402 of FIG. 4A. Cross-sectional view 404 taken along axis 402 of FIG. 4A is very similar to the cross-sectional view described at FIG. 3C with the exception that tube 108 of FIG. 4A includes an additional pilot line port 313.

Turning now to FIG. 5, FIG. 5 shows example cavity configurations 500 for the one or more cavities of the restrictor according to at least one example of the present disclosure. For viewing purposes, the cavity configurations 500 are shown in a segment of the restrictor, as opposed to showing the cavity configurations in a fully connected ring-shaped restrictor, for example. In at least one embodiment, the cavity configurations 500 may be formed into a restrictor such as restrictor 106, where the cavities of the cavity configurations 500 may correspond to the cavities 138 of the restrictor 106. Further, in at least one example the restrictor 106 may be a band. As such, restrictor 106 may also be referred to herein as a band.

The cavity configurations 500 comprise one or more cavities formed into the restrictor, where the restrictor is hollow and tubular in shape. In at least one embodiment, the cavity configurations may only comprise one cavity formed into the restrictor, which may be advantageous for simplifying the production of the restrictor and to avoid weakening the restrictor by including too many cavities. Furthermore, by reducing a number of cavities or a size of the cavities, leakage through the restrictor may be avoided. Alternatively, in other embodiments a cavity configuration may comprise more than one cavity in the restrictor in order to improve a flow rate through the restrictor for drainage purposes.

Different shapes may be possible for the one or more cavities formed into the restrictor. For example, shapes of the one or more openings formed into the restrictor may include longitudinal slits 502, horizontal slits 504, ovals 506, and circles 508. Other shapes such as stars, squares, triangles, etc. may also be possible. In some cases, different shapes for the openings may achieve different advantages. For example, the longitudinal slits 502 and the horizontal slits 504 may be particularly simple to produce. Regarding the ovals 506 and circles 508, benefits in regards to maintaining an integrity of the restrictor may be achieved.

In some examples where there may be more than one cavity formed into the restrictor, all of the cavities may be a same shape. However, in other examples where there may be more than one cavity formed into the restrictor, the cavities may vary in shape. Additionally or alternatively, in examples where there may be more than one cavity formed in a restrictor, a size of the cavities in the single restrictor may be varied. For example, a length of the longitudinal slits 502 may be varied. As another example, a width of the horizontal slits 504 may be varied. Such variety in one or more of a size and shape of the cavities in a same restrictor may be beneficial for improving drainage through the restrictor, in some examples.

Turning now to FIG. 6, FIG. 6 shows example cross-sections of a restrictor 600 according to at least one example of the present disclosure. In some examples, more than one of the example cross-sections 600 may be found in a same restrictor. However, in other examples, a single restrictor may correspond to only one cross-section of the example cross-sections for a restrictor 600. Further, more cross-sections in addition to the example cross-sections of a restrictor 600 shown in FIG. 6 may be possible.

It is noted that a positive x-axis 166 side of the cross-sections 600 of FIG. 6 corresponds to a region of the restrictor that is coupled with the ETT system (e.g., coupled with the inflatable cuff or coupled with the tube of the ETT system). The negative x-axis 166 side of the cross-sections correspond with a region of the restrictor that is opposite a side of the restrictor that is coupled with the ETT system, and the negative x-axis 166 side of the cross-sections face towards a collection region (e.g., collection region 126). In at least one example, the example cross-sections of a restrictor 700 may be cross-sections of a restrictor 106 as described above.

Turning to first example cross-section 602 of a restrictor, cross-section 602 comprises a single cavity 138 formed into restrictor wall 620. In particular, the cavity 138 opens through a first side of restrictor wall 620 and into an interior space 152 of the restrictor. Cavity 138 is proportionally large compared to the first side of the restrictor wall 620. A second side of restrictor wall 620 opposing the first side of the restrictor wall 620 is solid and does not comprise any cavities opening through the first side of the restrictor wall 620. Furthermore, a top and a bottom of restrictor wall 620 are also solid and without cavities formed through either the top or the bottom of restrictor wall 620.

A restrictor with an example cross-section 602 may be particularly advantageous for increasing a flow through the restrictor. For example, as cavity 138 is proportionally large compared to the height of the first side of restrictor wall 620, a relatively high flow rate of secretions may pass through the cavity 622. Additionally, cavity 138 being proportionally large compared the height of the first side of restrictor wall 620 may allow the passage of larger particles, in at least one embodiment.

Furthermore, in at least one example, the second side of restrictor wall 620 in example cross-section 602 may be the side of the restrictor wall 620 that is positioned against an inflatable cuff or a tube of the ETT system when coupling the restrictor to the ETT system. Positioning the second side of the restrictor wall 620 against the inflatable cuff or the tube of the ETT system, in combination with the proportionally large sized cavity 138 may be particularly beneficial, as a greater surface area may be available via the second side of the restrictor wall 620 for attaching the restrictor to the ETT system, while still enabling a high flow rate and the passage of large particles through the restrictor.

Regarding second example cross-section 604 of a restrictor, cross-section 604 includes a cavity 138 that opens through a first side of the restrictor wall 620 and opens into an interior space 152 of the restrictor. Cavity 138 may be proportionally small compared to a height of the first side of the restrictor wall 620, which may be beneficial to prevent leakage through the restrictor during restrictor drainage, for example. Additionally, cavity 138 being proportionally small compared to a height of the first side of the restrictor wall 620 may be beneficial to prevent larger particles from being suctioned through the restrictor that may clog the restrictor drainage line, for example.

Cavity 138 may be positioned near a bottom of the restrictor in at least one example. The positioning of cavity 138 near the bottom of the restrictor may be beneficial to enable drainage of secretions collected at an unsealed region of the inflatable cuff even when not very much has been collected, where the unsealed region of the inflatable cuff is positioned between the sealed regions of the inflatable cuff, the sealed regions being regions of contact between the inflatable cuff and a trachea wall of a patient. Put another way, the positioning of the cavity 138 to be near a bottom of the restrictor may enable suctioning of secretions collected even when a pool of secretions collected at the unsealed region is shallow. However, in other examples it may be possible for a positioning of the cavity 138 to instead be near a center of the restrictor or near a top of the restrictor.

Furthermore, similar to example cross-section 602 discussed above, a second side of restrictor wall 620 opposing the first side of the restrictor wall 620 may not include any openings that open through the second side of restrictor wall 620. By having the second side of restrictor wall 620 solid, such as shown in example cross-section 604, greater surface area may be available via the second wall for coupling such a point of the restrictor to the ETT system.

Turning now to a third example cross-section 606 of a restrictor, cross-section 606 includes multiple cavities 138 formed through restrictor wall 620, where each of the multiple cavities 138 open into a same interior space 152 of the restrictor. It is noted that in some examples that more or fewer openings than are shown in the third example cross-section 606 may be possible.

The cavities 138 may be located around an entire perimeter of restrictor. By including cavities around the entire perimeter of the restrictor that open into the interior space 152 of the restrictor, several advantages may be achieved. For example, the inclusion of openings around the entire perimeter of the restrictor may simplify positioning of the restrictor on the inflatable cuff, as the restrictor may be exposed to a collection region to enable drainage through the openings no matter how the restrictor is positioned over the inflatable cuff. Additionally, a high flow-rate may be achieved due to the multiple openings while the openings may still be made small enough to prevent large particles that may clog the restrictor drainage system from passing through the restrictor.

Regarding fourth example cross-section 608, the fourth example cross-section 608 is similar to cross-section 606 with the exception that openings are not included around an entire perimeter of the restrictor. Rather, cavities 138 are only included in the sides of the restrictor wall 620 and cavities are not included in a top and a bottom of the restrictor wall. By including openings in both sides of the restrictor wall 620 and by not including openings in the top and bottom of the restrictor wall 620, the strength of the restrictor may be increased compared to restrictors where openings may be included around an entire perimeter of the restrictor, while still achieving the advantages of a high flow rate. Further, the inclusion of openings in both sides of the restrictor wall 620 may simplify positioning of the restrictor over the inflatable cuff compared to examples where the restrictor includes openings on only one side of the restrictor wall.

Turning now to fifth example cross-section 610, rather than a single interior space, multiple separate interior spaces 152 are formed in the fifth example cross-section 610. Each of the separate interior spaces 152 of the fifth example cross-section 610 may correspond to multiple cavities 138 that are formed into the restrictor wall 620, and these multiple cavities 138 may only open into the separate interior space 152 to which they correspond. In particular, each of the separate interior spaces 152 may correspond to a pair of cavities 138, and the pair of cavities 138 may only open into the interior space 152 to which they correspond. The cavities 138 may be formed into two sides of the restrictor, which may be beneficial for simplifying a process of positioning the restrictor on the inflatable cuff or tube of the ETT system, as it may be easier to ensure that the openings face into the collection region to enable drainage through the restrictor.

The inclusion of multiple separate interior spaces 152 each corresponding to multiple openings may be beneficial to prevent clogging of the restrictor drainage system. In particular, as there are multiple separate interior spaces included in the restrictor, as long as at least one of the sets of cavities 138 and corresponding interior spaces 152 is clear (i.e., not blocked), the restrictor drainage system may be able to drain secretions through the restrictor.

In some examples more than one of the separate interior spaces 152 may open into a same larger interior space 152. For example, a restrictor may include a cross-section comprising multiple separate interior spaces as shown at fifth cross-section 610 that is adjacent to a cross-section comprising an interior space larger than the multiple separate interior spaces, and a group of the separate interior spaces may open into the larger interior space. The larger interior space may be connected to an restrictor drainage line to enable suction of secretions through the cavities 138 corresponding to the group of separate interior spaces, through each of the separate interior spaces 152 of the group of separate interior spaces 152, through the larger interior space that the group of separate interior spaces opens into, through the restrictor drainage line, and into the restrictor drainage bulb, for example. Such examples where multiple separate interior spaces that are each connected to a separate cavity 138 open into a larger interior space may be advantageous, as the multiple separate interior spaces 152 may function as a filter to prevent larger particles from being suctioned through the restrictor, while the larger interior space may still allow a high flow rate through the restrictor.

Additionally or alternatively, restrictors including multiple separate interior spaces may be connected to multiple restrictor drainage lines, where each of the separate interior spaces may be connected to a separate restrictor drainage line.

Turning now to sixth example cross-section 612, sixth example cross-section 612 of a restrictor is narrower and includes an interior space 152 that is narrower than the previously described cross-sections.

Restrictors where the cross-section 612 is narrow may be beneficial, as the narrow cross-section may help to form a larger collection region compared to restrictors with wide cross-sections. Thus more secretions may be held at the collection region in examples where the restrictor cross-section is narrow, since a larger collection region may be formed. It is noted that any one or combination of opening/interior space configurations described herein may be modified to be narrow to achieve the advantage of a larger collection region. As one example, sixth cross-section 612 is shown with a single cavity 138 formed into the side of restrictor wall 620 that faces the collection region and with a single cavity 138 formed into the side of restrictor wall 620 that is coupled with the inflatable cuff or tube of the ETT system. Both of the cavities 138 of cross-section 618 may be positioned near a bottom of the restrictor to enable drainage of secretions, even when there may not be a lot of secretions collected at the collection region.

Regarding seventh example cross-section 614, seventh example cross-section 614 is similar to fourth example cross section 608, with the exception that the cavities 138 are only formed into a side of the restrictor wall 620 that faces the collection region. By only forming the cavities 138 into the side of the restrictor wall 620 that faces the collection region, leakage through the restrictor may be prevented while still obtaining a high flow-rate through the restrictor. Additionally, a greater surface area for coupling the restrictor to the inflatable cuff or tube of the ETT system may be available compared to examples where openings are formed into both sides of the restrictor wall.

Turning now to eighth example cross-section 616, eighth example cross-section 616 only includes one cavity 138 that opens into an interior space 152 of the restrictor. The interior space 152 of eighth example cross-section 616 may be relatively small compared to the portion of eighth cross-section 616 that is restrictor wall 620. Thus, a majority of the eighth cross-section 616 comprises restrictor wall 620 and is solid, and a relatively small portion of the cross-section 616 is comprised of the interior space 152. Therefore, a majority of the restrictor may be solid. Such examples may be beneficial for preventing leakage through the restrictor and for overall strengthening of the restrictor.

Turning now to ninth example cross-section 618, ninth cross-section 618 is similar to fifth example cross-section 610 with the exception that only one cavity 138 opens into each of the separate interior spaces 152, where all of the cavities 138 are formed through a side of the restrictor wall 620 that faces collection region. This configuration may achieve several advantages. First, similar to other examples described above, by only forming openings into the side of the restrictor that faces the collection region, greater surface area of the restrictor may be available for coupling the restrictor to the inflatable cuff or tube of the ETT system and result in a stronger coupling between the restrictor and the inflatable cuff or tube of the ETT system. Additionally, the inclusion of multiple separate interior spaces 152 may help to avoid the restrictor from becoming blocked. For example, similar to examples discussed in relation to fifth cross-section 610, ninth cross-section 618 may be adjacent to a cross-section with a larger interior space, and the multiple separate interior spaces 152 of cross-section 618 may function as a filter to prevent clogging in the restrictor while also having the advantage of a high flow-rate due to the larger interior space. Additionally or alternatively, the inclusion of multiple separate interior spaces 152 may help to prevent blockage of the restrictor, since as long as at least one of the opening/separate interior space sets is clear (i.e., not blocked), drainage of secretions through the restrictor may still occur.

Turning now to FIG. 7, a flow chart for an example method 700 of operating an ETT system according to at least one embodiment of the disclosure is shown. It is noted that the ETT system of method 700 may be any one of the above discussed example ETT systems. Thus, features discussed above in relation to any one or combination of the above ETT systems may also apply to the steps of method 700.

Method 700 may begin at step 702, where an inflatable cuff is positioned on a tube (an ETT) of an ETT system. Positioning the inflatable cuff on the ETT may include positioning the inflatable cuff such that the inflatable cuff surrounds the tube. However, in some examples, positioning the inflatable cuff on the ETT may include positioning the inflatable cuff such that the inflatable cuff only partially surrounds the tube. In at least one example, positioning the inflatable cuff on the ETT may include positioning the inflatable cuff on the ETT such that the inflatable cuff is connected to pilot balloon via a pilot balloon line.

Following positioning the inflatable cuff on the ETT, method 700 may include performing an integrity and functionality check on the inflatable cuff at step 703. Performing the integrity and the functionality check on the inflatable cuff may include filling the inflatable cuff with saline solution or air to check for leaks in the inflatable cuff, for example. Filling the inflatable cuff with saline solution may include injecting saline solution through a one-way valve of the pilot balloon, through the pilot balloon, and through the pilot balloon line connecting the pilot balloon to the inflatable cuff, similar to the steps for inflating the inflatable cuff with air that are discussed above. In other examples, the inflatable cuff may be filled with fluids other than air or saline solution to check for an integrity of the inflatable cuff similar to the manner discussed above for inflating the inflatable cuff. It is noted that in at least one example, the integrity and functionality of the inflatable cuff may be checked prior to positioning the inflatable cuff on the ETT to avoid having to reposition another inflatable cuff on the ETT. However, in some cases it may be desirable to perform the integrity and functionality test on the inflatable cuff following positioning the inflatable cuff on the ETT to ensure that the inflatable cuff does not leak and functions properly after being manipulated to be positioned on the ETT.

If the inflatable cuff fails the integrity check at step 703, method 700 may move to step 704, where step 704 includes removing and replacing the inflatable cuff. For example, the inflatable cuff may fail the integrity check at 703 if the fluid used to test the integrity of the inflatable cuff leaks out of the inflatable cuff. The new inflatable cuff may then undergo an integrity and functionality test at step 703.

After checking the integrity of the inflatable cuff at step 703, if the inflatable cuff passes the integrity and functionality test, method 700 may include positioning a restrictor around the inflatable cuff at step 705. For example, in cases where the performing the integrity and functionality test at step 703 on the inflatable cuff may include injecting fluid into the inflatable cuff to check for leaks, the inflatable cuff may pass the integrity and functionality check if there are no leaks through the inflatable cuff. The restrictor positioned around the inflatable cuff at step 705 may include any one or combination of the features of the above discussed example restrictors. In at least one example, the restrictor may fully surround the inflatable cuff. However, in other examples, the restrictor may only surround a portion of the inflatable cuff. Additionally or alternatively, the restrictor may be positioned to surround the tube of the ETT system without an inflatable cuff coupled between the restrictor and the tube (ETT) of the ETT system. For example, a restrictor may additionally or alternatively be coupled directly to the tube of the ETT system between two separate inflatable cuffs.

Following positioning the restrictor band around the inflatable cuff (and/or around the tube of the ETT system), method 700 comprises performing an integrity and functionality test on a restrictor at step 706, including checking the integrity and functionality of the cavities of the restrictor. For example, an integrity and functionality of the restrictor may include connecting the restrictor to a restrictor drainage bulb (e.g., via a restrictor drainage line), and suctioning fluid through the restrictor and into the drainage bulb. The fluid may be saline solution or air, for example. In examples where saline solution may be suctioned through the restrictor to perform the integrity and functionality test of the restrictor, the restrictor may first be at least partially submerged in saline solution prior to applying suction via the restrictor drainage bulb.

The restrictor may pass the integrity and functionality test at step 706 if fluid is successfully suctioned through the restrictor into the drainage bulb. The restrictor may fail the integrity and functionality test at step 706 if the fluid is unsuccessfully suctioned through the restrictor into the drainage bulb or if less than a threshold amount of fluid is suctioned into the restrictor. If the restrictor fails the integrity and functionality test at step 706, the restrictor and/or a restrictor drainage line may be replaced or repositioned at step 707.

For example, it may be determined that there is a breach in the restrictor drainage line, and the restrictor drainage line may need to be replaced. Additionally or alternatively, it may be determined that the restrictor drainage line is not properly connected to one of the restrictor drainage bulb and the restrictor drainage line. In examples where the restrictor drainage line does not include any breaches and where the restrictor drainage line is simply improperly connected to one or both of the restrictor and restrictor drainage bulb, the restrictor drainage line may be repositioned to properly connect to the restrictor and/or restrictor drainage bulb.

Regarding the restrictor, it may be discovered that one or more of the cavities of the restrictor may have stretched to be too large to provide sufficient drainage, and the restrictor may need to be replaced. Additionally or alternatively, in examples where the cavity configuration of the restrictor only includes one or more cavities on a single side of the restrictor, it may be determined that the restrictor needs to be repositioned to properly align the one or more cavities of the restrictor to be open to the fluid. Following step 707, method 700 may proceed to step 705 where an integrity and functionality test may be performed on the newly replaced/repositioned restrictor.

Following the restrictor passing the integrity and functionality test at step 706, if the restrictor passes the integrity and functionality test at step 706, method 700 may include positioning the tube (ETT) of the ETT system in a trachea of a patient at step 708 to intubate the patient. In particular, the ETT may be positioned in a trachea of a patient such that the inflatable cuff positioned on the tube (ETT) may be aligned with the trachea. It is noted that the ETT may be positioned in the trachea of the patient while the inflatable cuff is in a deflated state, in at least one example. Positioning the ETT in the trachea of the patient while the inflatable cuff is deflated may make it easier to move the ETT system through the airway of the patient and make it easier to position the ETT in the trachea of the patient. This is not least because the ETT system may be more compact when in the deflated state than when the ETT system is in the inflated state.

Once the ETT is positioned in the trachea of the patient, the inflatable cuff of the ETT system may be inflated at step 709. For example, inflating the inflatable cuff may include inflating a single inflatable cuff of the ETT system. However, in other examples, multiple separate inflatable cuffs may be inflated. The inflatable cuff(s) may be inflated via any one or combination of the approaches described above. For example, inflating the inflatable cuff(s) of the ETT system may include introducing air into the inflatable cuff(s) via an inflation assembly such as the inflation assemblies described above that include a pilot balloon, a one-way valve, and a pilot line.

Moreover, at step 709, as the inflatable cuff(s) are inflated, a depression may be formed in a top of the inflatable cuff(s) at step 710. For example, the depression may be formed due to the inflatable cuff(s) curving upwards upon inflation. In embodiments where there may be multiple, separate inflatable cuffs, a depression may only be formed in a top of a most upstream inflatable cuff. However, in other examples where there may be multiple, separate inflatable cuffs, a depression may be formed in a top of each of the inflatable cuffs. The formation of a depression in a top of an inflatable cuff may enable passive collection of the secretions in the depression, and these secretions collected in the depression may be subsequently drained. The formation of a depression in the top of the inflatable cuff may be optional in at least one example. Thus, step 710 of method 700 is shown in dash.

Additionally, inflation of the inflatable cuff(s) may form a sealed region at step 712. The sealed region may be a region of contact between the inflatable cuff and the trachea wall of the patient.

In some examples, forming a sealed region may include forming a first sealed region and forming a second sealed region. In particular, as the inflatable cuff receives air, the inflatable cuff expands outward. Thus, in examples where the inflatable cuff has a restrictor coupled thereto, the inflatable cuff may expand at regions of the inflatable cuff both upstream and downstream the restrictor until these regions of the inflatable cuff upstream and downstream of the restrictor contact the trachea wall. The region of the inflatable cuff upstream of the restrictor may be a first protruding region of the inflatable cuff and the region of the inflatable cuff downstream of the restrictor may be a second protruding region of the inflatable cuff.

In examples where there may be multiple inflatable cuffs, each of the inflatable cuffs may expand and contact the trachea wall to form a corresponding sealed region. For example, if there ETT system included two separate inflatable cuffs, each of the inflatable cuffs may expand upon inflation to contact the trachea wall of the patient, forming two sealed regions.

Further, in at least one embodiment, only one sealed region may be formed. For example, in embodiments where the restrictor is coupled to an upper region of the inflatable cuff, upon inflation of the inflatable cuff, only a region of the inflatable cuff downstream the restrictor may expand enough to contact the trachea wall of the patient. Put another way, in examples where the restrictor may be positioned to surround an uppermost region of the inflatable cuff, the restrictor may restrict the uppermost region of the inflatable cuff from expanding enough during inflation of the inflatable cuff to contact the trachea wall of the patient, and only the region of the inflatable cuff downstream of the restrictor may expand sufficiently during inflation to contact the trachea wall of the patient. Thus, only one sealed region may be formed in such examples, and the inflatable cuff may have a generally triangular cross-sectional shape.

Additionally, upon inflation of the inflatable cuff, method 700 includes forming an unsealed region that includes a collection region at step 714.

For example, in embodiments where a restrictor may be positioned around the inflatable cuff, inflating the inflatable cuff may result in an unsealed region being formed between the first sealed region and the second sealed region. In particular, as the inflatable cuff is inflated, regions of the inflatable cuff upstream and downstream of the restrictor that is positioned around the inflatable cuff may expand to form a first sealed region and a second sealed region, respectively, and the restrictor may restrict expansion of the inflatable cuff at a location where the restrictor is positioned around the inflatable cuff.

Restricting expansion of the inflatable cuff at the location where the restrictor is positioned around the inflatable cuff thus results in the formation of an unsealed region between the first sealed region and the second sealed region, as the inflatable cuff may be prevented from contacting the trachea wall of the patient at the location where the restrictor is positioned on the inflatable cuff. This unsealed region may advantageously include a collection region for collecting secretions, as secretions that may leak downstream of the first sealed region may be trapped upstream of the second sealed region at the unsealed region.

Put another way, restricting expansion of the inflatable cuff during inflation at the location where the restrictor is positioned around the inflatable cuff may result in the inflatable cuff forming a valley between two protruding regions of the inflatable cuff. This valley of the inflatable cuff may not contact the trachea wall when the inflatable cuff is inflated, thus forming an unsealed region that includes a collection region for collecting secretions.

In embodiments where the ETT system may additionally or alternatively comprise multiple, separate inflatable cuffs, a region at the tube (the ETT) of the ETT system between the first inflatable cuff and the second inflatable cuff may form a valley upon expansion of the first inflatable cuff and the second inflatable cuff. A restrictor may be coupled to the tube of the ETT system between the first inflatable cuff and the second inflatable cuff in examples where there may be multiple, separate inflatable cuffs.

As such, in both examples where there may be multiple, separate inflatable cuffs, as well as examples where there may only be a single inflatable cuff, a restrictor may be coupled to the ETT system at an unsealed region that includes a collection region, where the unsealed region is formed between regions of the ETT system forming a first sealed region and a second sealed region. Such positioning of the restrictor at the unsealed region including the collection region may be advantageous to enable drainage of secretions, for example.

Furthermore, in examples such as discussed above where a restrictor may be coupled to an upper region of the inflatable cuff so that only a single sealed region is formed between the inflatable cuff and the trachea wall upon inflation of the inflatable cuff, inflation of the inflatable cuff may result in the formation of an unsealed region that includes a collection region. For example, the unsealed region of the inflatable cuff that includes the collection region may collect secretions upstream of the sealed region.

Turning now to step 716 of method 700, in examples where a depression is formed in the top of the inflatable cuff, as discussed at step 710, method 700 may include collecting secretions in the depression. For example, as the inflatable cuff is inflated, the inflatable cuff may curve upward such that the depression is formed in the top of the inflatable cuff. In particular, secretions may be passively collected in the depression due to gravity. Further, in embodiments where more than one inflatable cuff may include a depression formed in a top thereof, collecting secretions in the depression at step 716 may include collecting secretions in each of the depressions.

Following the collection of secretions in the depression at step 716, the secretions collected in the depression may be drained at step 718. For example, the secretions may be drained via suctioning the secretions from the depression with a suctioning device. In at least one example, the suctioning device may be a syringe. However, other suctioning devices may also be possible. It is noted that steps 716 and 718 are shown in dash, as steps 716 and 718 may only be included in examples where a depression is formed in a top of the inflatable cuff.

Turning now to step 720 of method 700, step 720 may include collecting secretions at the unsealed region. In particular, in embodiments where there may be a first sealed region and a second sealed region, as discussed above, secretions that may leak past the first sealed region may be trapped at the collection region, where the collection region may be included as a part of the unsealed region.

Thus, the formation of both sealed regions and an unsealed region when the inflatable cuff is inflated, where the unsealed region is positioned immediately and directly between two sealed regions, may be beneficial to prevent leakage of secretions into an airway of the patient. As such, aspiration may be avoided.

Additionally or alternatively, in examples where there may be multiple separate inflatable cuffs, and the unsealed region including the collection region may be located between the inflatable cuffs, collecting the secretions at step 720 may include trapping secretions that leak past the first inflatable cuff forming the first sealed region upstream of the second inflatable cuff forming the second sealed region.

Moreover, ETT systems that additionally or alternatively include the above described configuration of an inflatable cuff with a restrictor positioned around an upper region of the inflatable cuff may collect secretions upstream of the single sealed region formed between that inflatable cuff and the trachea wall. In particular, in such examples where the unsealed region is at the upper region of the inflatable cuff, and where there is a single sealed region formed only downstream of the restrictor, secretions may be collected at the unsealed region located upstream of the single sealed region.

Following the collection of secretions at the collection region, method 700 may include draining the secretions collected at the collection region at step 722. In at least one example, draining the secretions collected at the collection region may include draining the collected secretions through one or more cavities formed into the wall of the restrictor. In some examples, draining the collected secretions through the one of more cavities formed into the restrictor may include actively draining the secretions. Such active drainage may be performed in any one or combination of the approaches discussed above.

For example, in at least one embodiment, the secretions may be suctioned from the unsealed region that includes the collection region, through at least one of the one or more cavities formed through the wall of the restrictor, through a restrictor drainage line, and into a collection reservoir of a restrictor drainage bulb. The restrictor drainage bulb may then be subsequently emptied and replaced. Such suctioning may be achieved by compressing the restrictor drainage bulb while the restrictor drainage bulb is decoupled from the restrictor drainage line and coupling the restrictor drainage bulb to the restrictor drainage line while the restrictor drainage bulb is compressed. The restrictor drainage bulb may then decompress, thus applying a negative pressure to the unsealed region formed between the sealed off regions of the trachea that are formed by the inflatable cuff of the ETT system and causing secretions collected at the unsealed region to be drawn through the restrictor, the restrictor drainage line, and into the collection reservoir of the restrictor drainage bulb.

Following draining of the secretions collected at the unsealed region, the inflatable cuff may be deflated in at least one example to allow the removal of the ETT from the trachea of the patient.

Turning now to FIG. 8A, FIG. 8A shows a fifth example ETT system 800. It is noted that ETT system 800 may include any one or combination of features as described in relation to the previous example ETT systems.

As shown in ETT system 800, tail 176 connects restrictor 106 to the ETT 108 to fluidly connect the drainage bulb and the restrictor 106. In at least one example, a first end of tail 176 may be connected to a cavity 138 formed into the restrictor 106. Further, in at least one example, a second end of the tail 176 that is opposite the first end of the tail 176 may be connected to a restriction drainage line port of the ETT.

In at least one embodiment, the second end of the tail 176 may be connected to restriction drainage line port comprising a first section 316a, a second section 316b, and a third section 316c, where the first section of the restriction drainage line port 316a opens through the wall of the ETT 108. It is noted that cross-sections of the ETT system 800 shown in FIGS. 8B-8F illustrate the formation of the sections of the restrictor drainage line port into the wall of the ETT 108. Similarly, FIGS. 8B-8F also illustrate the formation of the inflation line port and the depression drainage line port.

In some examples, the tail 176 may be a tube that only connects the restrictor 106 to the third section of the restriction drainage line port 316c. In such examples where the tail 176 only connects restrictor 106 to the third section of the restriction drainage line port 316c, the tail 176 may open into the third section of the restrictor drainage line port 316c. The third section of the restrictor drainage line port 316c may then open into the second section of the restrictor drainage line port 316b, and the second section of the restrictor drainage line port 316b may open into the first section of the restrictor drainage line port 316a. The first section of the restrictor drainage line port 316a may then be coupled to the drainage bulb 124 via a restrictor drainage line 128. Thus, in such examples, secretions may be suctioned through the one or more cavities 138 of restrictor 106, through an interior space of the restrictor 106, through a tail 176, directly through the third, second, and first sections of the restrictor drainage line port (316c, 316b, 316a, respectively), through restrictor drainage line 128, and into the drainage bulb 124.

Alternatively, in some examples the tail 176 may be part of the restrictor drainage line 128 or directly coupled to the restrictor drainage line 128, and the restrictor drainage line 128 may be housed in the first, second, and third sections of the restrictor drainage line port. Thus, in such examples, secretions may be suctioned through a line housed in the restrictor drainage line port, as opposed to only through the restrictor drainage line port. Examples where secretions may be suctioned through a restrictor drainage line, as opposed to being directly suctioned through the restrictor drainage line port may be advantageous for sanitation purposes, as the restrictor drainage line may be replaced, in at least one example.

Regarding the first, second, and third sections of the restrictor drainage line port, in at least one example, the first section of the restriction drainage line port 316a may meet the second section of the restriction drainage line port 316b at approximately 90°. However, in other examples, the first section of the restriction drainage line port 316a may meet the second section of the restriction drainage line port 316b at an obtuse angle in order to reduce an amount of strain on restriction drainage line that may be housed in the restriction drainage line port.

The second section of the restriction drainage line port 316b may be an opening formed into the wall of the ETT 108 along a length of the ETT 108. Additionally, the second section of the restriction drainage line port 316b opens into a third section of the restriction drainage line port 316c, where the third section of the restriction drainage line port 316c opens through the wall of the ETT 108. In at least one example, the third section of the restriction drainage line port 316b may meet the second section of the restriction drainage line port 316b at approximately 90°. However, in other examples, the second section of the restriction drainage line port 316b may meet the third section of the restriction drainage line port 316c at an obtuse angle in order to reduce an amount of strain on restriction drainage line that may be housed in the restriction drainage line port.

Regarding the depression drainage line port, the depression drainage line port may also comprise a first section, a second section, and a third section, similar to the restriction drainage line port. The first section of the depression drainage line port 314a may open through a wall of the ETT 108, and the first section of the depression drainage line port 314a may further open into the second section of the depression drainage line port 314b. The second section of the depression drainage line port 314b may be circumferentially surrounded by the wall of the ETT 108, and the second section of the depression drainage line port 314b may run along a length of the ETT 108. The second section of the depression drainage line port 314b may open into the third section of the depression drainage line port 314c, where the third section of the depression drainage line port 314c opens through a wall of the ETT 108. In particular, the third section of depression drainage line port 314c may open near a depression that is formed into a top of the inflatable cuff 104 upon inflation of the inflatable cuff 104. Such positioning of the third section of the depression drainage line port 314c may enable secretions collected in the depression to be suctioned directly through the depression drainage line port 314c.

Furthermore, similar to the restrictor drainage line port, the depression drainage line port may house a line for suctioning secretions. For example, the depression drainage line port may house a depression drainage line 117, where the depression drainage line is connected to the depression drainage bulb 115. Thus secretions collected via depression may be drained through depression drainage line 117, where the depression drainage line 117 is housed the depression drainage line port. It is noted that, although not shown, in examples where a depression drainage line 117 is housed within the depression drainage line port, the depression drainage line 117 may extend through first, second, and third sections of the depression drainage line port 314a, 314b, 314c such that a portion of the depression drainage line 117 extends out of the opening formed into the wall of the ETT 108 at the third section of the restrictor drainage line port 314c. However, in other examples, the depression drainage line port may not house depression drainage line 117, and depression drainage line 117 may instead be coupled to the first section of the depression drainage line port 314a that opens through the wall of the ETT 108. In such examples, secretions drained from the depression may be suctioned directly through the third, second, and first sections of the depression drainage line port (314c, 314b, and 314a, respectively), through depression drainage line 117, and into depression drainage bulb 115.

Turning now to FIG. 8B, FIG. 8B shows a first cross-sectional view of the fifth example ETT system 820, taken along axis 802 of ETT system 800, as shown in FIG. 8A. As shown in FIG. 8B, tube 108 is solid at axis 802, and the tube does not comprise any ports formed into the wall of the tube 108 (i.e., ETT).

In regards to FIG. 8C, FIG. 8C shows a second cross-sectional view of the fifth example ETT system 822, taken along axis 804 of ETT system 800, as shown in FIG. 8A. It is noted that for viewing purposes, the portions of the depression drainage line, restrictor drainage line, and the pilot line that extend beyond the exterior of the tube 108 have been omitted in FIG. 8C and FIG. 8E.

As shown at FIG. 8C, the wall of tube 108 comprises ports. In particular, the wall of tube 108 comprises a first section the pilot line port 312a, a first section of the depression drainage line port 314, and a first section of the restrictor drainage line port 316a at axis 814, where the first section of the ports is a section that opens through a wall of the tube 108. In particular, the first section of the ports is a section of the ports that opens through an exterior surface of the wall of the tube 108, the exterior surface of the wall of the tube 108 being a surface of the wall of the tube 108 opposite an interior surface of the wall of the tube 108, where the interior surface of the wall of the tube 108 is a surface of the tube immediately surrounding and exposed to the internal space 210 of the tube 108. The internal space 210 of the tube 108 is continuously open through the entire length of the tube 108.

Furthermore, the first section of the ports (312a, 314a, 316a) open through the wall of the tube at an end of the tube 108 near the restrictor drainage bulb 124, pilot balloon 110, and depression drainage bulb 115. Though the first section of the ports are all shown opening through the wall of the tube 108 at a same point along a length of the tube 108, it is noted that in at least one example that the first section of ports may open through the wall of the tube 108 at different points along the length of the tube 108. Furthermore, though the ports are approximately symmetrically spaced apart around the circumference of tube 108 in FIG. 8C, asymmetrical spacing may also be possible.

In at least one example, one or all of the first sections of the ports may house lines. For example, the first section of the pilot line port 312a may house a pilot line 112. Additionally or alternatively, the first section of the restrictor drainage line port 316a may house a restrictor drainage line 128. Additionally or alternatively, the first section of the depression drainage line port may house depression drainage line 117. However, in at least one example, some or all of the ports may not house lines and the ports may instead simply be connected to the lines, such that the port itself forms a part of a passage for flowing various fluids through the ETT system. Thus, pilot line 112, restrictor drainage line 128, and depression drainage line 117 are schematically shown in dash, as in at least one example, some or all of these lines may not be housed in the ports formed into the wall of the tube 108.

Furthermore, in at least one example, more ports or fewer ports may be formed into the wall of the tube 108. For example, more ports may be formed into the wall of the tube 108 to accommodate additional lines, or more ports may be formed into the wall of the tube 108 to form additional passages for flowing various fluids through the ETT system. In examples where there may be fewer ports formed into the wall of the tube 108, the lines may be coupled to the ETT system in a different manner.

For example, lines may instead be attached to an exterior surface of the tube. Additionally or alternatively, the lines may instead be attached to an interior surface of the tube 108. In examples where one or more lines may instead be attached to an interior surface of the tube 108, the wall of the tube 108 may comprise an opening that passes through both the interior surface of the tube 108 and the exterior surface of the tube 108 for each line coupled to the interior of the tube 108 to enable suctioning of secretions or inflation of the inflatable cuff.

Turning now to FIG. 8D, FIG. 8D shows a third cross-section of the fifth example ETT system 824, taken along axis 806. The third cross-section of the fifth example ETT system 824 shows a view of the second section of the ports. In particular, the second section of the ports, including the second section of pilot line port 312b, the second section of depression drainage line port 314b, and restrictor drainage line port 316b are shown in the third cross-section of the fifth example ETT system 824. However, as discussed above, more or fewer ports may be included in at least one example.

The second section of the ports may be a portion of the ports that runs along a length of the tube 108, and the second section of the ports may connect the first section of the ports to the third section of the ports. In particular, the second section of the ports may open into the first section of the ports, and the second section of the ports may open into the third section of the ports, such that a continuous opening may be formed by the first, second and third sections of the ports formed into the wall of tube 108.

Turning now to FIG. 8E, FIG. 8E shows a fourth example cross-section of the fifth example ETT system 826, taken along axis 808. The fourth example cross-section of the fifth example ETT system 826 may comprise a third section of the restrictor drainage line port 316c and a third section of the depression drainage line port 314c, where the third section of the ports is a section where the port opens through an exterior wall of the tube. It is noted that although the third section of the restrictor drainage line port 316c and the third section of the depression drainage line port 314c are located at a same point along a length of the tube 108, in at least one example the third section of the depression drainage line port 314c and the third section of the restriction drainage line port 316c may be at different points along the length of the tube 108.

The third section of the pilot line port 312c (shown in FIG. 8F), where the pilot line port opens through the exterior surface of the tube 108 is positioned to be underneath an inflatable cuff to enable inflation of the inflatable cuff. Thus, as the fourth example cross-section of the fifth example ETT system 826 is taken along axis 316c, above the inflatable cuff 104, the second section of the pilot line port 312b is shown at FIG. 8E.

Turning to FIG. 8F, FIG. 8F shows a fifth example cross-section of the fifth example ETT system 828. Third section of the pilot line port 312c is shown in the fifth example cross-section of the fifth example ETT system 828, where the third section of the pilot line port 312c opens through the exterior surface of the wall of the tube 108. Further, the third section of the pilot line port 312c aligns with an opening in the wall of the inflatable cuff 106, thus fluidly coupling the lumen 206 of the inflatable cuff to enable inflation via the inflation assembly. In some examples, where the pilot line port houses a pilot line coupling the pilot balloon to the inflatable cuff, the pilot line may extend through the pilot line port formed into the tube and into the inflatable cuff.

It will be appreciated that the configurations and/or approaches described herein are exemplary in nature, and that these specific embodiments or examples are not to be considered in a limiting sense, because numerous variations are possible. The subject matter of the present disclosure includes all novel and nonobvious combinations and sub-combinations of the various features, functions, acts, and/or properties disclosed herein, as well as any and all equivalents thereof.

The invention claimed is:

1. An endotracheal tube (ETT) system, comprising:
a tube;
an inflatable cuff coupled to the tube; and
a restrictor comprising one or more cavities, the restrictor surrounding the tube, wherein the inflatable cuff is positioned between the restrictor and the tube, and wherein the restrictor restricts the inflatable cuff to form a valley positioned between two protruding regions of the inflatable cuff upon inflation of the inflatable cuff.

2. The system of claim 1, wherein each of the two protruding regions of the inflatable cuff is configured to contact a trachea wall to form a first sealed region and a second sealed region.

3. The system of claim 1, further comprising a restrictor drainage bulb coupled to the restrictor via a restrictor drainage line.

4. The system of claim 3, wherein a wall of the tube surrounds at least a portion of the restrictor drainage line.

5. The system of claim 1, further comprising another inflatable cuff coupled to the tube, wherein the restrictor is positioned between the inflatable cuffs.

6. The system of claim 5, wherein each of the inflatable cuffs is configured to form a sealed region within an airway of a patient upon inflation of both of the inflatable cuffs.

7. An endotracheal tube (ETT) system, comprising:
a tube;
an inflatable cuff surrounding the tube;
a restrictor surrounding an exterior surface of the inflatable cuff; and
a restrictor drainage assembly coupled to the restrictor, wherein the restrictor is a band,
wherein each of one or more openings included in the band open into an interior space of the band and wherein, when the inflatable cuff is in an inflated state,
a diameter of a first protruding region of the inflatable cuff that is upstream of the restrictor is greater than a diameter of the restrictor, and
a diameter of a second protruding region of the inflatable cuff that is downstream of the restrictor is greater than the diameter of the restrictor.

8. The system of claim 7, wherein the restrictor drainage assembly includes a restrictor drainage bulb and a restrictor drainage line, where a first end of the restrictor drainage line is coupled to the restrictor drainage bulb, and where a second end of the restrictor drainage line is coupled to the restrictor.

9. The system of claim 7, wherein expansion of the inflatable cuff is restricted by the restrictor upon inflation of the inflatable cuff.

10. An endotracheal tube (ETT) system, comprising:
a first tube;
an inflatable cuff surrounding the first tube;
a restrictor surrounding an exterior surface of the inflatable cuff comprising one or more cavities; and
a restrictor drainage assembly coupled to the restrictor, the restrictor drainage assembly comprising a restrictor drainage bulb,
wherein the inflatable cuff is positioned between the restrictor and the first tube, and wherein the restrictor restricts the inflatable cuff to form a valley positioned between two protruding regions of the inflatable cuff upon inflation of the inflatable cuff.

11. The ETT system of claim 10, wherein the restrictor drainage bulb is fluidly coupled to the restrictor via a restrictor drainage line, the restrictor drainage line directly coupled to the restrictor drainage bulb.

12. The ETT system of claim 11, wherein the restrictor drainage line is further coupled to a tail, wherein the tail is a second tube coupled to the restrictor.

13. The ETT system of claim 12, wherein the restrictor drainage line is housed in a restrictor drainage line port formed into a wall of the first tube, and wherein the restrictor drainage line is directly coupled to the tail.

14. The ETT system of claim 11, wherein the restrictor drainage line is coupled to a restrictor drainage line port.

15. The ETT system of claim 14, wherein the restrictor drainage line port is further coupled to a tail of the restrictor drainage assembly, wherein the tail is a second tube coupled between the restrictor and the restrictor drainage line port.

* * * * *